United States Patent
Miller et al.

(10) Patent No.: US 10,676,458 B2
(45) Date of Patent: Jun. 9, 2020

(54) ANTIDIABETIC BICYCLIC COMPOUNDS

(71) Applicant: Merck Sharp & Dohme Corp., Rahway, NJ (US)

(72) Inventors: Michael Miller, Scotch Plains, NJ (US); Harry R. Chobanian, Aberdeen, NJ (US)

(73) Assignee: Merch Sharp & Dohne Corp. Rahway, Rahway, NJ (US)

( * ) Notice: Subject to any disclaimer, the term of this patent is extended or adjusted under 35 U.S.C. 154(b) by 0 days.

(21) Appl. No.: 16/083,677

(22) PCT Filed: Mar. 24, 2017

(86) PCT No.: PCT/US2017/023939
§ 371 (c)(1),
(2) Date: Sep. 10, 2018

(87) PCT Pub. No.: WO2017/172505
PCT Pub. Date: Oct. 5, 2017

(65) Prior Publication Data
US 2019/0071412 A1   Mar. 7, 2019

Related U.S. Application Data

(60) Provisional application No. 62/314,445, filed on Mar. 29, 2016.

(51) Int. Cl.

| | |
|---|---|
| *C07D 215/14* | (2006.01) |
| *C07D 401/04* | (2006.01) |
| *C07D 201/00* | (2006.01) |
| *A61K 31/47* | (2006.01) |
| *A61K 31/4709* | (2006.01) |
| *A61K 31/4725* | (2006.01) |
| *A61K 31/538* | (2006.01) |
| *A61K 45/06* | (2006.01) |
| *C07D 265/36* | (2006.01) |
| *C07D 413/04* | (2006.01) |

(52) U.S. Cl.
CPC ............ *C07D 401/04* (2013.01); *A61K 31/47* (2013.01); *A61K 31/4709* (2013.01); *A61K 31/4725* (2013.01); *A61K 31/538* (2013.01); *A61K 45/06* (2013.01); *C07D 201/00* (2013.01); *C07D 215/14* (2013.01); *C07D 265/36* (2013.01); *C07D 413/04* (2013.01)

(58) Field of Classification Search
CPC .. C07D 401/04; C07D 413/04; C07D 265/36; C07D 215/14; C07D 201/00; A61K 45/06; A61K 31/4725; A61K 31/4709; A61K 31/47
USPC ....................................................... 546/152
See application file for complete search history.

(56) References Cited

U.S. PATENT DOCUMENTS

| 2014/0088077 A1 | 3/2014 | Schwink et al. |
| 2016/0002255 A1 | 1/2016 | Brockunier et al. |

FOREIGN PATENT DOCUMENTS

| GB | 2498976 A | 7/2013 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |

(Continued)

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

(Continued)

*Primary Examiner* — Taylor V Oh
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

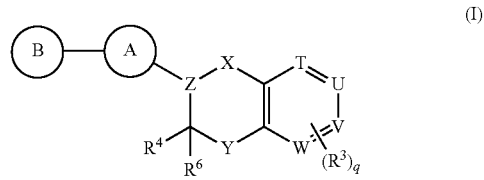

(I)

18 Claims, No Drawings

(56) References Cited

FOREIGN PATENT DOCUMENTS

| WO | WO2008030618 A1 | 3/2008 |
|---|---|---|
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012072691 A1 | 6/2012 |
| WO | WO2013122028 A1 | 8/2013 |
| WO | WO2013122029 A1 | 8/2013 |
| WO | 2015024448 A1 | 2/2015 |
| WO | WO2015024448 A1 | 2/2015 |
| WO | 2016019863 A1 | 2/2016 |
| WO | 2016022446 A1 | 2/2016 |
| WO | WO2016022448 A1 | 2/2016 |

OTHER PUBLICATIONS

Brown, S. P. et al., Discovery of AM-1638: A Potent and Orally Bioavailable GPR40/FFA1 Full Agonist, American Chemical Society, 2012, p. 726-730, vol. 3.

Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

International Search Report for PCT/US2017/023939 dated Jun. 19, 2017, 7 pages.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS One, 2011, p. 1-10, vol. 6, No. 11.

Lou, J. et al., A Potent Class of GPR40 Full Agonist Engages the EnteroInsular Axis to Promote Glucose Control in Rodents, PLOS One, 2012, p. 6-12, vol. 7, Issue 10.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

ANTIDIABETIC BICYCLIC COMPOUNDS

CROSS-REFERENCE TO RELATED APPLICATIONS

This application is a U.S. National Phase application under 35 U.S.C. § 371 of PCT Application PCT/US17/023939, filed Mar. 24, 2017, which claims priority from and the benefit of US Provisional Application U.S. Provisional Application No. U.S. Ser. No. 62/314,445 filed Mar. 29, 2016.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results induction and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); (5) inhibitors of incretin hormone degradation (DPP-4 inhibitors, such as sitagliptin, alogliptin, vildagliptin, linagliptin, denagliptin and saxagliptin); and SGLT2 inhibitors (canagliflozin, dapagliflozin and empagliflozin).

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature,* 422: 173 (2003); Briscoe, C. P. et al., *J. Biol. Chem.,* 278: 11303 (2003); Kotarsky, K. et al., *Biochem. Biophys. Res. Comm.,* 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, WO2015/024448, and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

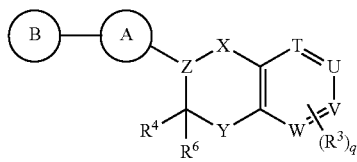

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

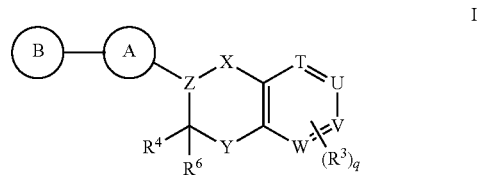

or a pharmaceutically acceptable salt thereof; wherein
T is selected from the group consisting of:
 (1) CH, and
 (2) N;
U is selected from the group consisting of:
 (1) $CR^1$, and
 (2) N;
V is selected from the group consisting of:
 (1) $CR^2$, and
 (2) N;
W is selected from the group consisting of:
 (1) CH, and
 (2) N,
provided that no more than two of T, U, V and W are N, further provided that if both T and W are N, then $R^3$ is absent, and further provided that both U and V are not N;
X is selected from the group consisting of:
 (1) $C(R^d)(R^d)$, and
 (2) $N(R^e)$;
Y is selected from the group consisting of:
 (1) oxygen,
 (2) $C(R^g)(R^g)$, and
 (3) $N(R^c)$;
Z is selected from the group consisting of:
 (1) $C(R^5)$, and
 (2) N,
provided that when X is $N(R^e)$, Z is not N, and further provided that when X is $C(R^d)(R^d)$, then Y is $C(R^g)(R^g)$;

A is selected from the group consisting of:
 (1) aryl,
 (2) heteroaryl,
 (3) $C_{3-8}$cycloalkyl, and
 (4) $C_{2-7}$cycloheteroalkyl,
wherein A is unsubstituted or substituted with one to five substituents selected from $R^a$; B is selected from the group consisting of:
 (1) aryl,
 (2) aryl-O—,
 (3) aryl-$C_{1-10}$ alkyl-,
 (4) aryl-$C_{1-10}$ alkyl-O—,
 (5) heteroaryl,
 (6) heteroaryl-O—,
 (7) heteroaryl-$C_{1-10}$ alkyl-, and
 (8) heteroaryl-$C_{1-10}$ alkyl-O—,
wherein B is unsubstituted or substituted with one to five substituents selected from $R^b$; $R^1$ and $R^2$ are each independently selected from:
 (1) hydrogen,
 (2) —$C_{1-6}$alkyl, and
 (3) —$C_{3-6}$cycloalkyl,
wherein each alkyl and cycloalkyl is substituted with a substituent selected from $R^7$ and with one to three substituents selected from $R^9$, provided that one of $R^1$ and $R^2$ is $C_{1-6}$alkyl or $C_{3-6}$cycloalkyl;
each $R^3$ is independently selected from the group consisting of:
 (1) hydrogen, and
 (2) F;
$R^4$ is selected from the group consisting of:
 (1) hydrogen,
 (2) halogen, and
 (3) $C_{1-6}$alkyl,
wherein alkyl is unsubstituted or substituted with one to three substituents selected from $R^h$;
$R^5$ is selected from the group consisting of:
 (1) hydrogen, and
 (2) —$C_{1-6}$alkyl,
wherein alkyl is unsubstituted or substituted with one to three substituents selected from $R^h$;
$R^6$ is selected from the group consisting of:
 (1) hydrogen, and
 (2) —$C_{1-6}$alkyl,
wherein alkyl is unsubstituted or substituted with one to three substituents selected from $R^h$;
$R^7$ is selected from the group consisting of:
 (1) —$CO_2R^8$, and
 (2) —$C_{1-6}$alkyl-$CO_2R^8$;
$R^8$ is selected from the group consisting of:
 (1) hydrogen, and
 (2) —$C_{1-6}$alkyl,
wherein alkyl is unsubstituted or substituted with one to three substituents selected from $R^i$;
each $R^9$ is independently selected from the group consisting of:
 (1) —$CO_2C_{1-6}$alkyl,
 (2) —$C_{1-10}$alkyl,
 (3) —$C_{2-10}$ alkenyl,
 (4) —$C_{2-10}$alkynyl,
 (5) —$C_{3-6}$cycloalkyl,
 (6) —$C_{2-6}$cycloheteroalkyl,
 (7) aryl, and
 (8) heteroaryl, wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;
each $R^a$ is selected from the group consisting of:
 (1) —$C_{1-6}$alkyl,
 (2) halogen,
 (3) —$C_{3-6}$cycloalkyl,
 (4) —$C_{2-5}$cycloheteroalkyl, and
 (5) —$C_{1-6}$alkylN($R^j$)($R^k$),
wherein each alkyl, cycloalkyl and cycloheteroalkyl is unsubstituted or substituted with one to three substituents independently selected from —$C_{1-6}$alkyl, halogen, —O—$C_{1-6}$alkyl, and —$CF_3$;
each $R^b$ is independently selected from the group consisting of:
 (1) —$C_{1-10}$alkyl,
 (2) —$CF_3$,
 (3) halogen,
 (4) —CN,
 (5) —OH, and
 (6) —$OC_{1-10}$alkyl,
wherein each alkyl is unsubstituted or substituted with one to three substituents independently selected from —$C_{1-6}$alkyl, halogen, —O—$C_{1-6}$alkyl, and —$CF_3$;
$R^c$ is independently selected from the group consisting of:
 (1) hydrogen,
 (2) $C_{1-10}$alkyl,
 (3) $C_{2-10}$alkenyl,
 (4) $C_{3-6}$cycloalkyl,
 (5) $C_{3-6}$ cycloalkyl-$C_{1-10}$alkyl-,
 (6) $C_{2-5}$cycloheteroalkyl, and
 (7) $C_{2-5}$cycloheteroalkyl-$C_{1-10}$alkyl-,
wherein alkyl, alkenyl, cycloalkyl, and cycloheteroalkyl is unsubstituted or substituted with one to three substituents independently selected from $R^f$;
each $R^d$ is selected from the group consisting of:
 (1) hydrogen,
 (2) —$C_{1-4}$alkyl, and
 (3) halogen,
wherein each alkyl is unsubstituted or substituted with one to five halogens;
$R^e$ is selected from the group consisting of:
 (1) hydrogen, and
 (2) —$C_{1-6}$alkyl,
wherein alkyl is unsubstituted or substituted with one to three substituents selected from —$C_{1-6}$alkyl, —$OC_{1-6}$alkyl, —$CF_3$ and halogen;
each $R^f$ is selected from the group consisting of:
 (1) —$C_{1-4}$alkyl,
 (2) —$OC_{1-4}$alkyl, and
 (3) halogen,
each $R^g$ is selected from the group consisting of:
 (1) hydrogen,
 (2) —$C_{1-4}$alkyl, and
 (3) halogen,
wherein each alkyl is unsubstituted or substituted with one to five halogens;
each $R^h$ is independently selected from the group consisting of:
 (1) —$C_{1-6}$alkyl,
 (2) —$OC_{1-6}$alkyl, and
 (3) halogen;
each $R^i$ is independently selected from the group consisting of:
 (1) —$C_{1-6}$alkyl,
 (2) —$OC_{1-6}$alkyl, and
 (3) halogen;

$R^j$ and $R^k$ are each independently selected from the group consisting of:
(1) hydrogen
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl, and
(7) $C_{2-5}$cycloheteroalkyl-$C_{1-10}$alkyl-,
wherein each alkyl, alkenyl, cycloalkyl, and cycloheteroalkyl is unsubstituted or substituted with one to three substituents independently selected from —$C_{1-6}$alkyl, halogen, or —O—$C_{1-6}$alkyl; and
q is independently selected from: 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, T is CH, U is $CR^1$, V is $CR^2$, and W is CH. In a class of this embodiment, T is CH, U is $CR^1$, V is CH, and W is CH. In another class of this embodiment, T is CH, U is CH, V is $CR^2$, and W is CH.

In another embodiment of the present invention, T is selected from the group consisting of: CH and N. In a class of this embodiment, T is CH. In another class of this embodiment, T is N. In another embodiment of the present invention, U is selected from the group consisting of: $CR^1$ and N. In a class of this embodiment, U is $CR^1$. In another class of this embodiment, U is N. In another embodiment of the present invention, V is selected from the group consisting of: $CR^2$ and N. In a class of this embodiment, V is $CR^2$. In another class of this embodiment, V is N.

In another embodiment of the present invention, W is selected from the group consisting of: CH and N, provided that no more than two of T, U, V and W are selected from N, further provided that if both T and W are N, then $R^3$ is absent, and further provided that both U and V are not N. In a class of this embodiment, W is CH, provided that no more than two of T, U and V are N, further provided that if two of T, U and V are N, then $R^3$ is absent, and further provided that both U and V are not N. In another class of this embodiment, W is N, provided that no more than two of T, U, V and W are N, further provided that if both T and W are N, then $R^3$ is absent, and further provided that both U and V are not N. In another class of this embodiment, W is N, provided that no more than two of T, U, V and W are N, further provided that if both T and W are N, then $R^3$ is absent, and further provided that both U and V are not N.

In another embodiment of the present invention, W is selected from the group consisting of: CH and N. In a class of this embodiment, W is CH. In another class of this embodiment, W is N.

In another embodiment of the present invention, T is N, U is $CR^1$, V is $CR^2$, and W is CH. In another embodiment of the present invention, T is CH, U is N, V is $CR^2$, and W is CH. In another embodiment of the present invention, T is CH, U is $CR^1$, and V is N, and W is CH. In another embodiment of the present invention, T is CH, U is $CR^1$, V is $CR^2$, and W is N. In another embodiment of the present invention, T is N, U is N, V is $CR^2$, and W is CH. In another embodiment of the present invention, T is N, U is $CR^1$, V is N, and W is CH. In another embodiment of the present invention, T is N, U is $CR^1$, V is $CR^2$, and W is N. In another embodiment of the present invention, T is N, U is $CR^1$, V is $CR^2$, and W is N; and $R^3$ is absent. In another embodiment of the present invention, T is CH, U is N, V is $CR^2$, and W is N. In another embodiment of the present invention, T is CH, U is $CR^1$, V is N, and W is N. In another embodiment of the present invention, T is CH; U is $CR^1$; V is $CR^2$; and W is CH or N.

In another embodiment of the present invention, X is selected from the group consisting of: $C(R^d)(R^d)$, and $N(R^e)$. In a class of this embodiment of the present invention, X is selected from the group consisting of: $CH_2$, NH, and $NCH_3$.

In another embodiment of the present invention, X is selected from the group consisting of: $N(R^e)$. In a class of this embodiment of the present invention, X is selected from the group consisting of: NH, and $NCH_3$.

In another embodiment of the present invention, Y is selected from the group consisting of: oxygen, $C(R^g)(R^g)$, and $N(R^c)$.

In another embodiment of the present invention, Y is selected from the group consisting of: oxygen, and $C(R^g)(R^g)$. In a class of this embodiment of the present invention, Y is selected from the group consisting of: oxygen, and $CH_2$.

In another embodiment of the present invention, Y is oxygen.

In another embodiment of the present invention, Y is selected from the group consisting of: $C(R^g)(R^g)$. In a class of this embodiment, Y is-$CH_2$.

In another embodiment of the present invention, Z is selected from the group consisting of: $C(R^5)$, and N, provided that when X is $N(R^e)$, Z is not N, and further provided that when X is $C(R^d)(R^d)$, then Y is $C(R^g)(R^g)$. In a class of this embodiment of the present invention, Z is selected from the group consisting of: CH, and N, provided that when X is $N(R^e)$, Z is not N, and further provided that when X is $C(R^d)(R^d)$, then Y is $C(R^g)(R^g)$.

In another embodiment of the present invention, Z is selected from the group consisting of: $C(R^5)$ provided that when X is $C(R^d)(R^d)$, then Y is $C(R^g)(R^g)$. In a class of this embodiment of the present invention, Z is CH, provided that when X is $C(R^d)(R^d)$, then Y is $C(R^g)(R^g)$.

In another embodiment of the present invention, Z is N, provided that X is not $N(R^e)$, and further provided that when X is $C(R^d)(R^d)$, then Y is $C(R^g)(R^g)$.

In another embodiment of the present invention, A is selected from the group consisting of: aryl, heteroaryl, $C_{3-8}$cycloalkyl, and $C_{2-7}$cycloheteroalkyl, wherein A is unsubstituted or substituted with one to five substituents selected from $R^a$.

In another embodiment of the present invention, A is selected from the group consisting of: aryl, and $C_{2-7}$cycloheteroalkyl, wherein aryl and cycloheteroalkyl are unsubstituted or substituted with one to five substituents selected from $R^a$. In a class of this embodiment, A is selected from the group consisting of: phenyl and piperidine, wherein phenyl and piperidine are unsubstituted or substituted with one to five substituents selected from $R^a$.

In another embodiment of the present invention, A is aryl, wherein aryl is unsubstituted or substituted with one to five substituents selected from $R^a$. In a class of this embodiment, A is phenyl, wherein phenyl is unsubstituted or substituted with one to five substituents selected from $R^a$.

In another embodiment of the present invention, A is selected from the group consisting of: $C_{2-7}$cycloheteroalkyl, wherein cycloheteroalkyl is unsubstituted or substituted with one to five substituents selected from $R^a$. In a class of this embodiment, A is piperidine, wherein piperidine is unsubstituted or substituted with one to five substituents selected from $R^a$.

In another embodiment of the present invention, B is selected from the group consisting of: aryl, aryl-O—, aryl-$C_{1-10}$ alkyl-, aryl-$C_{1-10}$ alkyl-O—, heteroaryl, heteroaryl-O, heteroaryl-$C_{1-10}$ alkyl-, and heteroaryl-$C_{1-10}$ alkyl-O—, wherein B is unsubstituted or substituted with one to five substituents selected from $R^b$.

In another embodiment of the present invention, B is selected from the group consisting of: aryl, aryl-$C_{1-10}$ alkyl-, heteroaryl, and heteroaryl-$C_{1-10}$ alkyl-, wherein B is unsubstituted or substituted with one to five substituents selected from $R^b$.

In another embodiment of the present invention, B is selected from the group consisting of: aryl, and aryl-$C_{1-10}$ alkyl-, wherein B is unsubstituted or substituted with one to five substituents selected from $R^b$. In a class of this embodiment, B is selected from the group consisting of: phenyl, and phenyl-$CH_2$—, wherein B is unsubstituted or substituted with one to five substituents selected from $R^b$.

In another embodiment of the present invention, B is selected from the group consisting of: aryl, wherein aryl is unsubstituted or substituted with one to five substituents selected from $R^b$. In a class of this embodiment, B is phenyl, wherein phenyl is unsubstituted or substituted with one to five substituents selected from $R^b$.

In another embodiment of the present invention, B is selected from the group consisting of: aryl-$C_{1-10}$ alkyl-, wherein B is unsubstituted or substituted with one to five substituents selected from $R^b$. In a class of this embodiment, B is phenyl-$CH_2$—, wherein B is unsubstituted or substituted with one to five substituents selected from $R^b$.

In another embodiment of the present invention, $R^1$ and $R^2$ are each independently selected from: hydrogen, —$C_{1-6}$alkyl, and —$C_{3-6}$cycloalkyl, wherein alkyl and cycloalkyl is substituted with a substituent selected from $R^7$ and with one to three substituents selected from $R^9$, provided that one of $R^1$ and $R^2$ is $C_{1-6}$alkyl or $C_{3-6}$cycloalkyl. In a class of this embodiment, one of $R^1$ and $R^2$ is —$C_{1-6}$alkyl substituted with a substituent selected from $R^7$ and with one to two substituents selected from $R^9$, or —$C_{3-6}$cycloalkyl substituted with a substituent selected from $R^7$ and with one to two substituents selected from $R^9$.

In another embodiment of the present invention, $R^1$ and $R^2$ are each independently selected from: hydrogen, and —$C_{1-6}$alkyl, wherein alkyl is substituted with a substituent selected from $R^7$ and substituted with one to three substituents selected from $R^9$, provided that one of $R^1$ and $R^2$ is —$C_{1-6}$alkyl. In a class of this embodiment, $R^1$ and $R^2$ are each independently selected from: hydrogen, and —$C_{1-6}$alkyl, wherein alkyl is substituted with a substituent selected from $R^7$ and substituted with one to two substituents selected from $R^9$, provided that one of $R^1$ and $R^2$ is —$C_{1-6}$alkyl.

In another embodiment of the present invention, $R^1$ and $R^2$ are each independently selected from: hydrogen, and —$C_2$alkyl, wherein alkyl is substituted with a substituent selected from $R^7$ and substituted with one to three substituents selected from $R^9$, provided that one of $R^1$ and $R^2$ is —$C_2$alkyl. In a class of this embodiment, $R^1$ and $R^2$ are each independently selected from: hydrogen, and —$C_2$alkyl, wherein alkyl is substituted with a substituent selected from $R^7$ and substituted with one to two substituents selected from $R^9$, provided that one of $R^1$ and $R^2$ is —$C_2$alkyl.

In another embodiment, $R^1$ is —$C_{1-6}$alkyl, wherein alkyl is substituted with a substituent selected from $R^7$ and substituted with one to three substituents selected from $R^9$. In a class of this embodiment, $R^1$ is —$C_2$alkyl, wherein alkyl is substituted with a substituent selected from $R^7$ and substituted with two substituents selected from $R^9$.

In another embodiment, $R^1$ is —$C_{1-6}$alkyl, wherein alkyl is substituted with a substituent selected from $R^7$ and substituted with one to three substituents selected from $R^9$; and $R^2$ is hydrogen. In a class of this embodiment, $R^1$ is —$C_2$alkyl, wherein alkyl is substituted with a substituent selected from $R^7$ and substituted with two substituents selected from $R^9$; and $R^2$ is hydrogen.

In another embodiment of the present invention, $R^1$ is hydrogen.

In another embodiment, $R^2$ is —$C_{1-6}$alkyl, wherein alkyl is substituted with a substituent selected from $R^7$ and substituted with one to three substituents selected from $R^9$. In a class of this embodiment, $R^2$ is —$C_2$alkyl, wherein alkyl is substituted with a substituent selected from $R^7$ and substituted with two substituents selected from $R^9$.

In another embodiment, $R^2$ is —$C_{1-6}$alkyl, wherein alkyl is substituted with a substituent selected from $R^7$ and substituted with one to three substituents selected from $R^9$; and $R^1$ is hydrogen. In a class of this embodiment, $R^2$ is —$C_2$alkyl, wherein alkyl is substituted with a substituent selected from $R^7$ and substituted with two substituents selected from $R^9$; and $R^1$ is hydrogen.

In another embodiment of the present invention, $R^2$ is hydrogen.

In another embodiment of the present invention, when present, each $R^3$ is independently selected from the group consisting of: hydrogen, and F.

In another embodiment of the present invention, when present, $R^3$ is hydrogen.

In another embodiment of the present invention, when present, each $R^3$ is F.

In another embodiment of the present invention, $R^4$ is selected from the group consisting of: hydrogen, halogen, and —$C_{1-6}$alkyl, wherein alkyl is unsubstituted or substituted with one to three substituents selected from $R^h$.

In another embodiment of the present invention, $R^4$ is selected from the group consisting of: hydrogen, and —$C_{1-6}$ alkyl, wherein alkyl is unsubstituted or substituted with one to three substituents selected from $R^h$. In a class of this embodiment, $R^4$ is $C_{1-6}$alkyl, wherein alkyl is unsubstituted or substituted with one to three substituents selected from $R^h$. In another class of this embodiment, $R^4$ is hydrogen.

In another embodiment of the present invention, $R^4$ is selected from the group consisting of: hydrogen, and halogen. In a class of this embodiment, $R^4$ is halogen.

In another embodiment of the present invention, $R^5$ is selected from the group consisting of: hydrogen, and —$C_{1-6}$ alkyl, wherein alkyl is unsubstituted or substituted with one to three substituents selected from $R^h$. In a class of this embodiment, $R^5$ is $C_{1-6}$alkyl, wherein alkyl is unsubstituted or substituted with one to three substituents selected from $R^h$.

In another class of this embodiment, $R^5$ is hydrogen.

In another embodiment of the present invention, $R^6$ is selected from the group consisting of: hydrogen, and —$C_{1-6}$ alkyl, wherein alkyl is unsubstituted or substituted with one to three substituents selected from $R^h$. In a class of this embodiment, $R^6$ is $C_{1-6}$alkyl, wherein alkyl is unsubstituted or substituted with one to three substituents selected from $R^h$.

In another class of this embodiment, $R^6$ is hydrogen.

In another embodiment of the present invention, $R^7$ is selected from the group consisting of: $-CO_2R^8$, and $-C_{1-6}$alkyl-$CO_2R^8$.

In another embodiment of the present invention, $R^7$ is selected from the group consisting of: $-C_{1-6}$alkyl-$CO_2R^8$.

In another embodiment of the present invention, $R^7$ is $-CO_2R^8$. In a class of this embodiment, $R^7$ is $-CO_2H$.

In another embodiment of the present invention, $R^8$ is selected from the group consisting of: hydrogen, and $-C_{1-6}$alkyl, wherein alkyl is unsubstituted or substituted with one to three substituents selected from $R^i$.

In another embodiment of the present invention, $R^8$ is selected from the group consisting of: $-C_{1-6}$alkyl, wherein alkyl is unsubstituted or substituted with one to three substituents selected from $R^i$.

In another embodiment of the present invention, $R^8$ is hydrogen.

In another embodiment of the present invention, each $R^9$ is independently selected from the group consisting of: $-CO_2C_{1-6}$alkyl, $-C_{1-10}$alkyl, $-C_{2-10}$ alkenyl, $-C_{2-10}$ alkynyl, $-C_{3-6}$cycloalkyl, $-C_{2-6}$cycloheteroalkyl, aryl, and heteroaryl, wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and $-OC_{1-6}$alkyl.

In another embodiment of the present invention, each $R^9$ is independently selected from the group consisting of: $-CO_2C_{1-6}$alkyl, $-C_{1-10}$alkyl, $-C_{2-10}$ alkenyl, $-C_{2-10}$ alkynyl, $-C_{3-6}$cycloalkyl, and $-C_{2-6}$cycloheteroalkyl, wherein each alkyl, alkenyl, alkynyl, cycloalkyl, and cycloheteroalkyl is unsubstituted or substituted with 1-4 substituents selected from $C_{1-6}$alkyl, halogen, and $-OC_{1-6}$alkyl.

In another embodiment of the present invention, each $R^9$ is independently selected from the group consisting of: $-C_{1-10}$alkyl, $-C_{2-10}$ alkenyl, $-C_{2-10}$alkynyl, $-C_{3-6}$cycloalkyl, and $-C_{2-6}$cycloheteroalkyl, wherein each alkyl, alkenyl, alkynyl, cycloalkyl, and cycloheteroalkyl is unsubstituted or substituted with 1-4 substituents selected from $C_{1-6}$alkyl, halogen, and $-OC_{1-6}$alkyl.

In another embodiment of the present invention, each $R^9$ is independently selected from the group consisting of: $-C_{1-10}$alkyl, $-C_{2-10}$alkynyl, and $-C_{3-6}$cycloalkyl, wherein each alkyl, alkynyl, and cycloalkyl is unsubstituted or substituted with 1-4 substituents selected from $C_{1-6}$alkyl, halogen, and $-OC_{1-6}$alkyl.

In another embodiment of the present invention, each $R^9$ is independently selected from the group consisting of: $-C_{1-10}$alkyl, and $-C_{3-6}$cycloalkyl, wherein each alkyl and cycloalkyl is unsubstituted or substituted with 1-4 substituents selected from $C_{1-6}$alkyl, halogen, and $-OC_{1-6}$alkyl. In a class of this embodiment, each $R^9$ is independently selected from the group consisting of: $-C_{1-4}$alkyl, and $-C_{3-5}$cycloalkyl, wherein each alkyl and cycloalkyl is unsubstituted or substituted with 1-4 substituents selected from $C_{1-6}$alkyl, halogen, and $-OC_{1-6}$alkyl. In another class of this embodiment, each $R^9$ is independently selected from the group consisting of: $-C_{1-4}$alkyl, and $-C_{3-5}$cycloalkyl. In another class of this embodiment, each $R^9$ is independently selected from the group consisting of: $-CH_3$, and -cyclopropyl, wherein each $-CH_3$ and cyclopropyl is unsubstituted or substituted with 1-4 substituents selected from $C_{1-6}$alkyl, halogen, and $-OC_{1-6}$alkyl. In another class of this embodiment, each $R^9$ is independently selected from the group consisting of: $-CH_3$, and -cyclopropyl.

In another embodiment of the present invention, each $R^9$ is $-C_{1-10}$alkyl, wherein each alkyl is unsubstituted or substituted with 1-4 substituents selected from $C_{1-6}$alkyl, halogen, and $-OC_{1-6}$alkyl.

In a class of this embodiment, each $R^9$ is $-C_{1-4}$alkyl, wherein each alkyl is unsubstituted or substituted with 1-4 substituents selected from $C_{1-6}$alkyl, halogen, and $-OC_{1-6}$alkyl. In another class of this embodiment, each $R^9$ is $-C_{1-4}$alkyl. In another class of this embodiment, each $R^9$ is $CH_3$, wherein each $-CH_3$ is unsubstituted or substituted with 1-4 substituents selected from $C_{1-6}$alkyl, halogen, and $-OC_{1-6}$alkyl. In another class of this embodiment, each $R^9$ is $-CH_3$.

In another embodiment of the present invention, each $R^9$ is $-C_{3-6}$cycloalkyl, wherein each cycloalkyl is unsubstituted or substituted with 1-4 substituents selected from $C_{1-6}$alkyl, halogen, and $-OC_{1-6}$alkyl.

In a class of this embodiment, each $R^9$ is $-C_{3-5}$cycloalkyl, wherein cycloalkyl is unsubstituted or substituted with 1-4 substituents selected from $C_{1-6}$alkyl, halogen, and $-OC_{1-6}$alkyl. In another class of this embodiment, each $R^9$ is $-C_{3-5}$cycloalkyl. In another class of this embodiment, each $R^9$ is cyclopropyl is unsubstituted or substituted with 1-4 substituents selected from $C_{1-6}$alkyl, halogen, and $-OC_{1-6}$alkyl. In another class of this embodiment, each $R^9$ is cyclopropyl.

In another embodiment of the present invention, each $R^a$ is selected from the group consisting of: $-C_{1-6}$alkyl, halogen, $-C_{3-6}$cycloalkyl, $-C_{2-5}$cycloheteroalkyl, and $-C_{1-6}$alkylN($R^j$)($R^k$), wherein each alkyl, cycloalkyl and cycloheteroalkyl is unsubstituted or substituted with one to three substituents independently selected from $-C_{1-6}$alkyl, halogen, $-O-C_{1-6}$alkyl, and $-CF_3$.

In another embodiment of the present invention, each $R^a$ is selected from the group consisting of: $-C_{1-6}$alkyl, halogen, $-C_{3-6}$cycloalkyl, and $-C_{2-5}$cycloheteroalkyl; wherein each alkyl, cycloalkyl and cycloheteroalkyl is unsubstituted or substituted with one to three substituents independently selected from $-C_{1-6}$alkyl, halogen, $-O-C_{1-6}$alkyl and $-CF_3$.

In another embodiment of the present invention, each $R^a$ is selected from the group consisting of: $-C_{1-6}$alkyl, and halogen, wherein each alkyl is unsubstituted or substituted with one to three substituents independently selected from $-C_{1-6}$alkyl, halogen, $-O-C_{1-6}$alkyl and $-CF_3$.

In another embodiment of the present invention, each $R^a$ is $-C_{1-6}$alkyl, wherein each alkyl is unsubstituted or substituted with one to three substituents independently selected from $-C_{1-6}$alkyl, halogen, $-O-C_{1-6}$alkyl and $-CF_3$. In a class of this embodiment, each $R^a$ is $-C_{1-6}$alkyl.

In another embodiment of the present invention, each $R^a$ is halogen.

In another embodiment of the present invention, each $R^b$ is independently selected from the group consisting of: $-C_{1-10}$alkyl, $-CF_3$, halogen, $-CN$, $-OH$, and $-OC_{1-10}$alkyl, wherein each alkyl is unsubstituted or substituted with one to three substituents independently selected from $-C_{1-6}$alkyl, halogen, $-O-C_{1-6}$alkyl and $-CF_3$.

In another embodiment of the present invention, each $R^b$ is independently selected from the group consisting of: $-C_{1-10}$alkyl, $-CF_3$, halogen, and $-OC_{1-10}$alkyl, wherein each alkyl is unsubstituted or substituted with one to three substituents independently selected from $-C_{1-6}$alkyl, halogen, $-O-C_{1-6}$alkyl and $-CF_3$.

In another embodiment of the present invention, each $R^b$ is independently selected from the group consisting of: —$CF_3$, halogen, and —$OC_{1-10}$alkyl, wherein each alkyl is unsubstituted or substituted with one to three substituents independently selected from —$C_1$-6alkyl, halogen, —O—$C_{1-6}$alkyl and —$CF_3$. In a class of this embodiment, each $R^b$ is independently selected from the group consisting of: —$CF_3$, F, and —$OCH_3$.

In another embodiment of the present invention, each $R^b$ is —$CF_3$.

In another embodiment of the present invention, each $R^b$ is independently selected from the group consisting of: halogen, and —$OC_{1-10}$alkyl, wherein each alkyl is unsubstituted or substituted with one to three substituents independently selected from —$C_1$-6alkyl, halogen, —O—$C_{1-6}$alkyl and —$CF_3$. In a class of this embodiment, each $R^b$ is independently selected from the group consisting of: F, and —$OCH_3$.

In another embodiment of the present invention, $R^c$ is independently selected from the group consisting of: hydrogen, $C_{1-10}$alkyl, $C_{2-10}$alkenyl, $C_{3-6}$cycloalkyl, $C_{3-6}$cycloalkyl-$C_{1-10}$alkyl-, $C_{2-5}$cycloheteroalkyl, and $C_{2-5}$cycloheteroalkyl-$C_{1-10}$alkyl, wherein alkyl, alkenyl, cycloalkyl, and cycloheteroalkyl is unsubstituted or substituted with one to three substituents independently selected from $R^f$.

In another embodiment of the present invention, $R^c$ is independently selected from the group consisting of: hydrogen, —$C_{1-10}$alkyl, and $C_{2-10}$alkenyl, wherein alkyl, and alkenyl is unsubstituted or substituted with one to three substituents independently selected from $R^f$.

In another embodiment of the present invention, $R^c$ is independently selected from the group consisting of: hydrogen, and —$C_{1-10}$alkyl, wherein alkyl is unsubstituted or substituted with one to three substituents independently selected from $R^f$. In a class of this embodiment, $R^c$ is hydrogen. In another class of this embodiment, $R^c$ is —$C_{1-10}$alkyl, wherein alkyl is unsubstituted or substituted with one to three substituents independently selected from $R^f$. In another class of this embodiment, $R^c$ is —$C_{1-10}$alkyl.

In another embodiment of the present invention, each $R^d$ is selected from the group consisting of: hydrogen, —$C_{1-4}$alkyl, and halogen, wherein each alkyl is unsubstituted or substituted with one to five halogens.

In another embodiment of the present invention, each $R^d$ is selected from the group consisting of: hydrogen, and halogen. In a class of this embodiment, each $R^d$ is halogen.

In another embodiment of the present invention, each $R^d$ is selected from the group consisting of: hydrogen, and —$C_{1-4}$alkyl, wherein each alkyl is unsubstituted or substituted with one to five halogens. In a class of this embodiment of the present invention, each $R^d$ is selected from the group consisting of: hydrogen, and —$C_{1-4}$alkyl.

In another embodiment of the present invention, each $R^d$ is hydrogen.

In another embodiment of the present invention, each $R^d$ is —$C_{1-4}$alkyl, wherein each alkyl is unsubstituted or substituted with one to five halogens. In a class of this embodiment of the present invention, each $R^d$ is —$C_{1-4}$alkyl.

In another embodiment of the present invention, $R^e$ is selected from the group consisting of: hydrogen, and —$C_{1-6}$alkyl, wherein alkyl is unsubstituted or substituted with one to three substituents selected from —$C_{1-6}$alkyl, —$OC_{1-6}$alkyl, —$CF_3$ and halogen. In a class of this embodiment, $R^e$ is selected from the group consisting of: hydrogen, and —$C_1$-6alkyl.

In another embodiment of the present invention, $R^e$ is hydrogen.

In another embodiment of the present invention, $R^e$ is —$C_{1-6}$alkyl, wherein alkyl is unsubstituted or substituted with one to three substituents selected from —$C_{1-6}$alkyl, —$OC_{1-6}$alkyl, —$CF_3$ and halogen. In another class of this embodiment, $R^e$ is —$CH_3$.

In another embodiment of the present invention, each $R^f$ is selected from the group consisting of: —$C_{1-4}$alkyl, —$OC_{1-4}$alkyl, and halogen.

In another embodiment of the present invention, each $R^f$ is selected from the group consisting of: —$C_{1-4}$alkyl and halogen.

In another embodiment of the present invention, each $R^f$ is —$OC_{1-4}$alkyl.

In another embodiment of the present invention, each $R^f$ is —$C_{1-4}$alkyl.

In another embodiment of the present invention, each $R^f$ is halogen.

In another embodiment of the present invention, each $R^g$ is selected from the group consisting of: hydrogen, —$C_{1-4}$alkyl, and halogen, wherein each alkyl is unsubstituted or substituted with one to five halogens.

In another embodiment of the present invention, each $R^g$ is selected from the group consisting of: hydrogen, and halogen. In a class of this embodiment, each $R^g$ is halogen.

In another embodiment of the present invention, each $R^g$ is selected from the group consisting of: hydrogen, and —$C_{1-4}$alkyl, wherein each alkyl is unsubstituted or substituted with one to five halogens. In a class of this embodiment of the present invention, each $R^g$ is selected from the group consisting of: hydrogen, and —$C_{1-4}$alkyl.

In another embodiment of the present invention, each $R^g$ is hydrogen.

In another embodiment of the present invention, each $R^g$ is —$C_{1-4}$alkyl, wherein each alkyl is unsubstituted or substituted with one to five halogens. In a class of this embodiment of the present invention, each $R^g$ is —$C_{1-4}$alkyl.

In another embodiment of the present invention, each $R^h$ is independently selected from the group consisting of: —$C_{1-6}$alkyl, —$OC_{1-6}$alkyl, and halogen.

In another embodiment of the present invention, each $R^h$ is —$C_{1-6}$alkyl.

In another embodiment of the present invention, each $R^h$ is independently selected from the group consisting of: —$OC_{1-6}$alkyl, and halogen.

In another embodiment of the present invention, each $R^h$ is —$OC_{1-6}$alkyl.

In another embodiment of the present invention, each $R^h$ is halogen.

In another embodiment of the present invention, each $R^i$ is independently selected from the group consisting of: —$C_{1-6}$alkyl, —$OC_{1-6}$alkyl, and halogen.

In another embodiment of the present invention, each $R^i$ is —$C_{1-6}$alkyl.

In another embodiment of the present invention, each $R^i$ is independently selected from the group consisting of: —$OC_{1-6}$alkyl, and halogen.

In another embodiment of the present invention, each $R^i$ is —$OC_{1-6}$alkyl.

In another embodiment of the present invention, each $R^i$ is halogen.

In another embodiment of the present invention, $R^j$ is selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, and $C_{2-5}$cycloheteroalkyl-$C_{1-10}$alkyl-, wherein each alkyl, alkenyl, cycloalkyl and cycloheteroalkyl is unsubstituted or substituted with one to three substituents independently selected from —$C_{1-6}$alkyl, halogen, or —O—$C_{1-6}$alkyl.

In another embodiment of the present invention, $R^j$ is selected from the group consisting of: hydrogen, $C_{1-10}$alkyl, $C_{2-10}$alkenyl, $C_{3-6}$cycloalkyl, and $C_{2-5}$cycloheteroalkyl, wherein alkyl, alkenyl, cycloalkyl and cycloheteroalkyl is unsubstituted or substituted with one to three substituents independently selected from —$C_{1-6}$alkyl, halogen, or —O—$C_{1-6}$alkyl.

In another embodiment of the present invention, $R^j$ is selected from the group consisting of: hydrogen, and $C_{1-10}$alkyl, wherein alkyl is unsubstituted or substituted with one to three substituents independently selected from —$C_{1-6}$alkyl, halogen, or —O—$C_{1-6}$alkyl.

In another embodiment of the present invention, $R^j$ is —$C_{1-10}$alkyl, wherein alkyl is unsubstituted or substituted with one to three substituents independently selected from —$C_{1-6}$alkyl, halogen, or —O—$C_{1-6}$alkyl. In a class of this embodiment, $R^j$ is —$C_{1-10}$alkyl.

In another embodiment of the present invention, $R^j$ is hydrogen.

In another embodiment of the present invention, $R^k$ is selected from the group consisting of: hydrogen, $C_{1-10}$alkyl, $C_{2-10}$alkenyl, $C_{3-6}$cycloalkyl, $C_{3-6}$ cycloalkyl-$C_{1-10}$alkyl-, $C_{2-5}$cycloheteroalkyl, and $C_{2-5}$cycloheteroalkyl-$C_{1-10}$alkyl-, wherein alkyl, alkenyl, cycloalkyl, and cycloheteroalkyl are unsubstituted or substituted with one to three substituents independently selected from —$C_{1-6}$alkyl, halogen, or —O—$C_{1-6}$alkyl.

In another embodiment of the present invention, $R^k$ is selected from the group consisting of: hydrogen, $C_{1-10}$alkyl, $C_{2-10}$alkenyl, $C_{3-6}$cycloalkyl, and $C_{2-5}$cycloheteroalkyl, wherein alkyl, alkenyl, cycloalkyl, and cycloheteroalkyl are unsubstituted or substituted with one to three substituents independently selected from —$C_{1-6}$alkyl, halogen, or —O—$C_{1-6}$alkyl.

In another embodiment of the present invention, $R^k$ is selected from the group consisting of: hydrogen, and $C_{1-10}$alkyl, wherein alkyl is unsubstituted or substituted with one to three substituents independently selected from —$C_{1-6}$alkyl, halogen, or —O—$C_{1-6}$alkyl.

In another embodiment of the present invention, $R^k$ is —$C_{1-10}$alkyl, wherein alkyl is unsubstituted or substituted with one to three substituents independently selected from —$C_1$-6alkyl, halogen, or —O—$C_{1-6}$alkyl. In a class of this embodiment, $R^k$ is —$C_{1-10}$alkyl.

In another embodiment of the present invention, $R^k$ is hydrogen.

In another embodiment of the present invention, q is 0, 1, 2 or 3. In another embodiment of the present invention, q is 1, 2 or 3. In another embodiment of the present invention, q is 0, 1 or 2. In a class of this embodiment, q is 0 or 1. In another class of this embodiment, q is 1 or 2. In another class of this embodiment, q is 0. In another class of this embodiment, q is 1. In another class of this embodiment, q is 2. In another class of this embodiment, q is 3.

In another embodiment of the present invention, the invention relates to compounds of structural formula Ia:

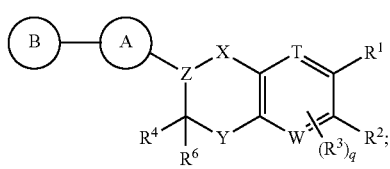

Ia or a pharmaceutically acceptable salt thereof.

In another embodiment of the present invention, the invention relates to compounds of structural formula Ib:

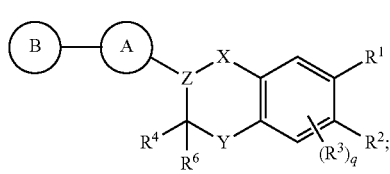

Ib or a pharmaceutically acceptable salt thereof.

In another embodiment of the present invention, the invention relates to compounds of structural formula Ic:

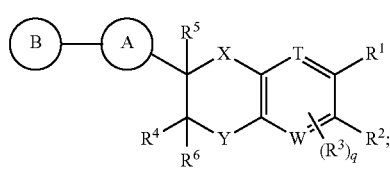

Ic or a pharmaceutically acceptable salt thereof.

In another embodiment of the present invention, the invention relates to compounds of structural formula Id:

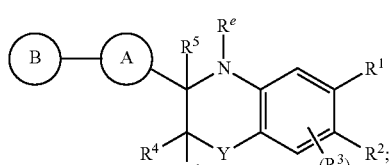

Id or a pharmaceutically acceptable salt thereof.

In another embodiment of the present invention, the invention relates to compounds of structural formula Ie:

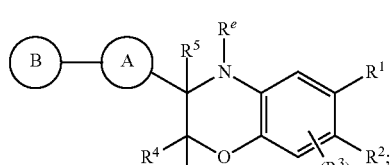

Ie or a pharmaceutically acceptable salt thereof.

In another embodiment of the present invention, the invention relates to compounds of structural formula If:

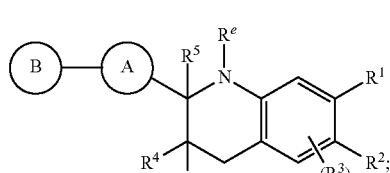

If or a pharmaceutically acceptable salt thereof.

In another embodiment of the present invention, the invention relates to compounds of structural formula Ig:

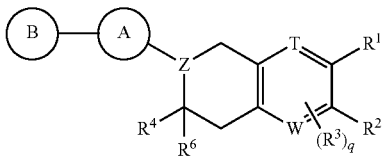

Ig or a pharmaceutically acceptable salt thereof.

In another embodiment of the present invention, the invention relates to compounds of structural formula Ih:

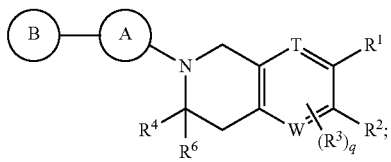

Ih or a pharmaceutically acceptable salt thereof.

In another embodiment of the present invention, the invention relates to compounds of structural formula Ii:

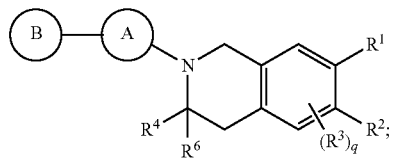

Ii or a pharmaceutically acceptable salt thereof.

The compound of structural formula I includes the compounds of structural formulas Ia, Ib, Ic, Id, Ie, If, Ig, Ih, and Ii, and pharmaceutically acceptable salts, hydrates and solvates thereof.

Another embodiment of the present invention relates to compounds of structural formula Id:

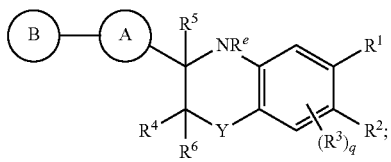

Id wherein
Y is selected from the group consisting of:
(1) oxygen, and
(2) —$CR^gR^g$;
A is selected from the group consisting of:
(1) aryl, and
(2) $C_{2-7}$cycloheteroalkyl,
wherein aryl and cycloheteroalkyl are unsubstituted or substituted with one to five substituents selected from $R^a$;

B is selected from the group consisting of:
(1) aryl, and
(2) aryl-$C_{1-10}$ alkyl-,
wherein B is unsubstituted or substituted with one to five substituents selected from $R^b$;
$R^1$ and $R^2$ are each independently selected from:
(1) hydrogen, and
(2) —$C_{1-6}$alkyl,
wherein each alkyl is substituted with a substituent selected from $R^7$ and with one to three substituents selected from $R^9$, provided that one of $R^1$ and $R^2$ is $C_{1-6}$alkyl;
$R^3$, $R^4$, $R^5$, $R^6$, and $R^8$ are hydrogen;
$R^7$ is —$CO_2R^8$;
each $R^9$ is independently selected from the group consisting of:
(1) —$C_{1-10}$alkyl, and
(2) —$C_{3-6}$cycloalkyl,
wherein each alkyl and cycloalkyl is unsubstituted or substituted with 1-4 substituents selected from $C_{1-6}$alkyl, halogen, and —$OC_{1-6}$alkyl;
$R^e$ is selected from the group consisting of:
(1) hydrogen, and
(2) —$C_{1-6}$alkyl,
wherein each alkyl is unsubstituted or substituted with one to three substituents selected from —$C_{1-6}$alkyl, —$OC_{1-6}$alkyl, —$CF_3$ and halogen; and
q is 1;
or a pharmaceutically acceptable salt thereof.

Another embodiment of the present invention relates to compounds of structural Formula Id:

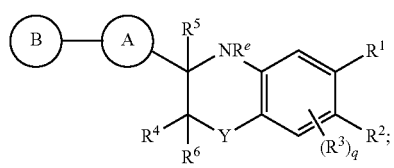

Id wherein
Y is selected from the group consisting of:
(1) oxygen, and
(2) —$CR^gR^g$;
A is aryl, wherein aryl is unsubstituted or substituted with one to five substituents selected from $R^a$;
B is aryl, wherein aryl is unsubstituted or substituted with one to five substituents selected from $R^b$;
$R^1$ is —$C_{1-6}$alkyl, wherein alkyl is substituted with a substituent selected from $R^7$ and with one to three substituents selected from $R^9$;
$R^2$, $R^3$, $R^4$, $R^5$, $R^6$, and $R^8$ are hydrogen;
$R^7$ is —$CO_2R^8$;
each $R^9$ is independently selected from the group consisting of:
(1) —$C_{1-10}$alkyl, and
(2) —$C_{3-6}$cycloalkyl,
wherein each alkyl and cycloalkyl is unsubstituted or substituted with 1-4 substituents selected from $C_{1-6}$alkyl, halogen, and —$OC_{1-6}$alkyl;
$R^e$ is selected from the group consisting of:
(1) hydrogen, and
(2) —$C_{1-6}$alkyl; and
q is 1;
or a pharmaceutically acceptable salt thereof.

Another embodiment of the present invention relates to compounds of structural Formula Ii:

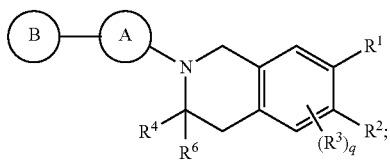

wherein
A is $C_{2-7}$cycloheteroalkyl, wherein cycloheteroalkyl is unsubstituted or substituted with one to five substituents selected from $R^a$;
B is aryl-$C_{1-10}$ alkyl-, wherein B is unsubstituted or substituted with one to five substituents selected from $R^b$;
$R^1$ is —$C_{1-6}$alkyl, wherein alkyl is substituted with a substituent selected from $R^7$ and with one to three substituents selected from $R^9$;
$R^2$, $R^3$, $R^4$, $R^6$, and $R^8$ are hydrogen;
$R^7$ is —$CO_2R^8$;
each $R^9$ is independently selected from the group consisting of:
  (1) —$C_{1-10}$alkyl, and
  (2) —$C_{3-6}$cycloalkyl,
wherein each alkyl and cycloalkyl is unsubstituted or substituted with 1-4 substituents selected from $C_{1-6}$alkyl, halogen, and —$OC_{1-6}$alkyl; and
q is 1;
or a pharmaceutically acceptable salt thereof.

Illustrative, but non-limiting, examples of the compounds of the present invention that are useful as agonists of G-protein-coupled receptor 40 (GPR40) are the following compounds:

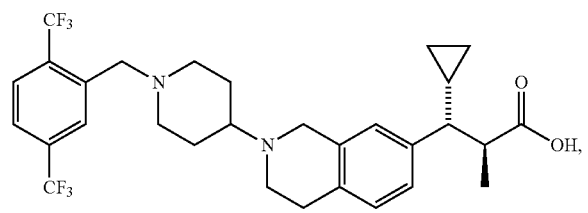

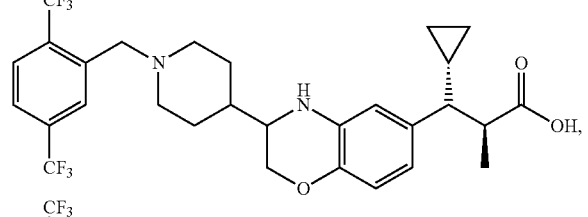

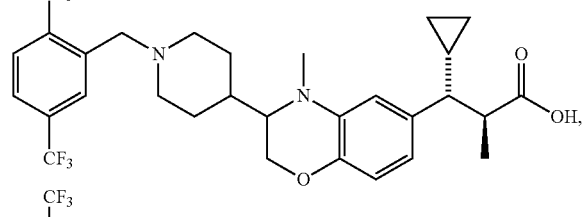

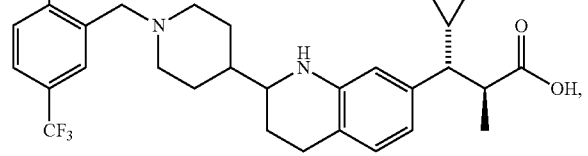

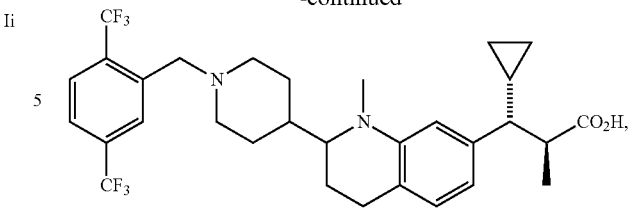

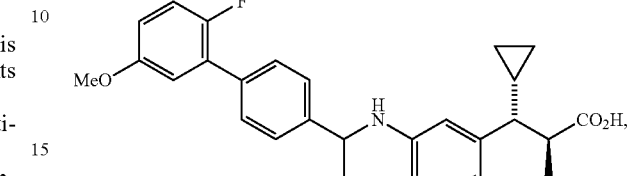

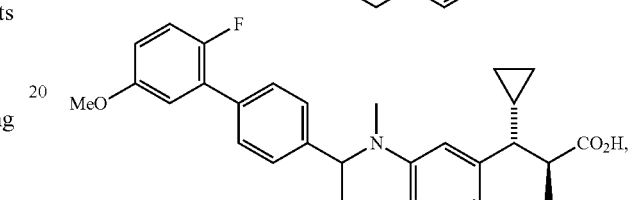

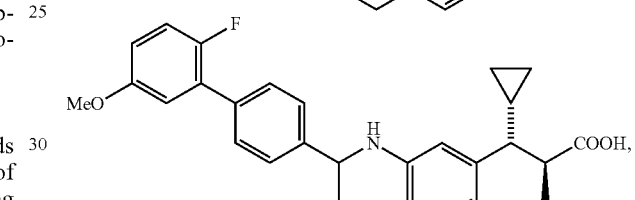

and

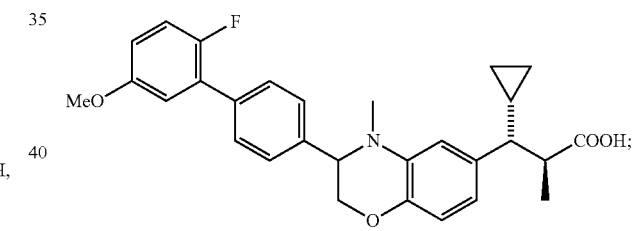

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)$—.
"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, alkynyl is —$C_2$alkyne-$CH_3$.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is cyclopropane.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cyclopentenyl.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1, 4:3, 6-dianhydromannitol, 1, 4:3, 6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: hexose, pentose, isosorbide and isomannide. In another embodiment of the present invention, cycloheteroalkyl is selected from: isosorbide and isomannide. In another embodiment of of the present invention, cycloheteroalkyl is selected from: oxetane, tetrahydropyran, azetidine, tetrahydrothiopyran and pyrrolidine. In another embodiment of the present invention cycloheteroalkyl is selected from: oxetane, -piperazine, azetidine, pyrrolidine, morpholine and spiro(indene-1,4-piperidine).

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl. In another embodiment of the present invention, aryl-O— is phenyl-O—. In another embodiment of the present invention, aryl-$C_{1-10}$alkyl-O— is phenyl-$CH_2$—O—.

"Heteroaryl" means monocyclic, bicyclic or tricyclic ring or ring system containing 2-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine, isoxazole, pyrimidine, thiazole, benzimidazole, benzthiazole, benzoxazole, and benzisoxazole. In another embodiment of the present invention, heteroaryl is selected from: pyridine, isoxazole and benzpyrazole. In another embodiment of the present invention, heteroaryl is pyridine or thiazole. In another embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

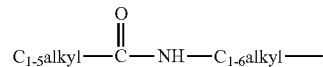

For example, —$NR^cC(O)R^e$ is equivalent to —$N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular the hydrates, of the compounds of the present invention are included in the present invention as well.

Utilities

The compounds of the present invention are potent agonists of the GPR40 receptor.

The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:
(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:
(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occur in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq 140$ mmHg/$\geq 90$ mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e., cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID 1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GPO10, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/ 0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATI-802, E3080, and the like; (26) camitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl) phenyl)-methoxy)phenyl)iso, 5-(4-((3-(2-methyl-6-(3-hydroxypropoxy)pyridine-3-yl)-2-methylphenyl)methoxy) phenyl)-isothiazole-3-ol 1-oxide, and 5-[4-[[3-[4-(3-aminopropoxy)-2,6-dimethylphenyl]phenyl]-methoxy] phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARt agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/

MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacinbound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, and the like; (29) IBAT inhibitors such as BARI143/HMR145A/HMR1453 (Sanofi-Aventis), PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) a/(3 adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl) carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vemalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech); and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone 3 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene; and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) McSr (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

List of Abbreviations

Ac is acetyl; AcCN is acetonitrile; AcO is acetoxy; AcOH is acetic acid; Alk is alkyl; anh. is anhydrous; APCI is atmospheric pressure chemical ionization; aq or aq. is aqueous; Ar is aryl; atm is atmosphere; Boc is tert-butoxycarbonyl; Bn-O is phenyl-$CH_2$—O or benzyloxy; Br is broad; n-BuLi is n-butyl lithium; $Bu_3P$ is tributylphosphine; t-BuOK is potassium tert-butoxide; ° C. is degrees celsius; Cbz is benzyloxycarbonyl; $CH_2Cl_2$ is dichloromethane; conc or conc. is concentrated; CV is column volumes; d is doublet; DAST is (diethylamino)sulfur trifluoride; DIBAL-H ix diisobutylaluminum hydride; DIAD is diisopropyl azodicarboxylate; DCM is dichloromethane; DEA is diethyl amine; DIPEA is N,N-diisopropylethylamine; DIPA is diisopropyl amine; DMAP is 4-dimethylaminopyridine; DMF is N,N-dimethylformamide; DMS is dimethyl sulfide; DMSO is dimethylsulfoxide; dppf is 1,1'-Bis(diphenyl-phosphino)ferrocene; ESI is electrospray ionization; EA or EtOAc is ethyl acetate; Et is ethyl; $Et_2O$ is diethyl ether; $Et_3N$ is triethyl amine; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; Josiphos is (S)-1-[(rp)-2-(di-tert-butyl phosphino)-ferrocenyl]ethyldiphenylphosphine or (2S)-1-[(1S)-1-[Bis(1,1-dimethylethyl)phosphino]-ethyl]-2-(diphenyl-phosphino)ferrocene; KOAc is potassium acetate; KOtBu is potassium tert-butoxide; L is liter; LAH is lithium aluminum hydride; M is molar; LC-MS is liquid chromatography-mass spectroscopy; LDA is lithium diisopropyl amide; m is multiplet; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeOH is methyl alcohol or methanol; $MgSO_4$ is magnesium sulfate; MPLC is medium pressure liquid chromatography; MS is mass spectroscopy; MsCl or Ms—Cl is methane sulfonyl chloride; MeCN is acetonitrile; MeI is methyl iodide; MsCl is methane sulfonyl chloride; MeCN is acetonitrile; Mpa is megapascal; MTBE is methyl tert-butyl ether; N is normal; $Na(AcO)_3BH$ is sodium triacetoxy borohydride; NaHMDS is sodium hexamethyl disilazide; NaOH is sodium hydroxide; $Na_2SO_4$ is sodium sulfate; $NH_4OAc$ is ammonium acetate; NBS is N-bromo succinamide; $NEt_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; paraform is paraform-aldehyde; PE is petroleum ether; PG is protecting group; i-PrOH is isopropanol; $Pd_2(dba)_3$ is tris(dibenzylidene-acetone)-dipalladium(0); $Pd(OAc)_2$ is palladium acetate; Pd $Cl_2$(dppf) is [1,1'-bis(diphenylphosphino)-ferrocene]dichloro-palladium (II); $Pd(PPh_3)_2Cl_2$ is bis(triphenylphosphine)palladium(II) dichloride; $PPh_3$ is triphenyl phosphine; prep is preparative; prep. TLC or prep-TLC, or prep TCL is preparative thin layer chromatography; rt or r.t. or RT isroom temperature; $R_f$ is retention factor; s is singlet; sat or sat. is saturated; SEM is trimethylsilyl ethoxy methyl, SEMCl is trimethylsilyl ethoxy methyl chloride; SFC is supercritical fluid chromatography; t is triplet; TBAF is tetrabutylammonium fluoride; TBSCl is tert-butyl dimethylsilyl chloride; TEA is triethyl amine; Tf is trifluoromethane sulfonyl; THF is tetrahydrofuran; $Ti(OiPr)_4$ is titanium isopropoxide; TFA is trifluoroacetic acid; TLC is thin-layer chromatography; TosCl and TsCl is p-toluene sulfonyl chloride; pTSA, pTsOH and TsOH is p-toluenesulfonic acid, and $Ts_2O$ is tosic anhydride orp-toluene sulfonic anhydride.

Several methods for preparing the compounds of this invention are illustrated in the following Schemes, Intermediates and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided for the purpose of illustration only and are not to be construed as limitations on the disclosed invention. All temperatures are degrees Celsius unless otherwise noted.

Intermediate 1

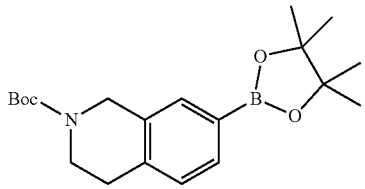 [SMILES: CC(C)(C)OC(=O)N1CCc2ccc(B3OC(C)(C)C(C)(C)O3)cc2C1]

tert-Butyl-7-(4,4,5,5-tetramethyl-1,3,2-dioxaborolan-2-yl)-3,4-dihydroisoquinoline-2 (1H)-carboxylate)

A mixture of bis-pinacolatodiboron (325 mg, 1.3 mmol), tert-butyl-7-bromo-3,4-dihydroisoquinoline-2(1H)-carboxylate (200 mg, 0.6 mmol), KOAc (189 mg, 1.9 mmol) and PdCl$_2$(dppf) (94 mg, 0.13 mmol) in DMSO (2 mL) was stirred at 60° C. for 3 h. Then the reaction mixture was cooled to rt and diluted with water (30 mL). The resulting mixture was extracted with EtOAc (30 mL×3). The combined organic layers were washed with brine (30 mL), dried over anhydrous Na$_2$SO$_4$ and filtered. The filtrate was concentrated under reduced pressure to give the title compound. MS (ESI) m/z: 345 [M-t-butyl+MeCN+H]$^+$.

Intermediate 2

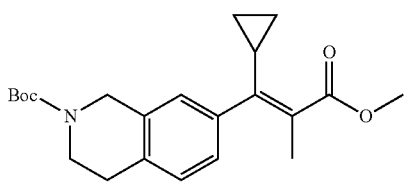 [SMILES: COC(=O)/C(C)=C(/c1ccc2c(c1)CN(C(=O)OC(C)(C)C)CC2)C1CC1]

(E)-tert-Butyl 7-(1-cyclopropyl-3-methoxy-2-methyl-3-oxoprop-1-en-1-yl)-3,4-dihydroisoquinoline-2(1H)-carboxylate A mixture of Pd(PPh$_3$)$_2$Cl$_2$ (6 mg, 8.3 μmol), K$_2$CO$_3$ (23 mg, 0.17 mmol), (Z)-methyl-3-cyclopropyl-2-methyl-3-(tosyloxy)-acrylate (31 mg, 0.1 mmol) and Intermediate 1 (30.0 mg, 0.08 mmol) in THF (2.5 mL) and H$_2$O (0.5 mL) was stirred at 80° C. for 1 h. Then the reaction was cooled to rt and water (20 mL) was added to the reaction. The aqueous phase was extracted with EtOAc (20 mL×3). The combined organic layers were washed with brine (40 mL), dried over anhydrous MgSO$_4$ and filtered. The filtrate was concentrated under reduced pressure. The resulting residue was purified by prep-TLC (SiO$_2$, PE:EtOAc=5:1, v/v) to give the title compound. $^1$H NMR (400 MHz, CDCl$_3$): δ 7.01 (d, J=7.7 Hz, 1H), 6.77 (d, J=7.7 Hz, 1H), 6.69 (s, 1H), 4.51 (br. s., 2H), 3.63 (br. s., 2H), 3.40 (s, 3H), 2.79 (br. s., 2H), 2.13 (s, 3H), 1.89-1.79 (m, 1H), 1.48 (s, 9H), 0.77-0.69 (m, 2H), 0.38-0.23 (m, 2H).

Intermediate 3

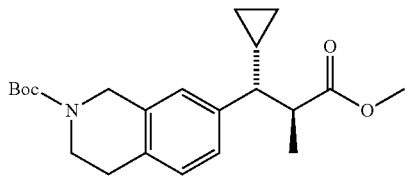 [SMILES: COC(=O)[C@@H](C)[C@H](c1ccc2c(c1)CN(C(=O)OC(C)(C)C)CC2)C1CC1]

tert-Butyl 7-((1R,2S)-1-cyclopropyl-3-methoxy-2-methyl-3-oxopropyl)-3,4-dihydroisoquinoline-2 (1H)-carboxylate To a solution of intermediate 2 (470 mg, 1.3 mmol) in DCM (0.5 mL) and MeOH (5 mL) was added Josiphos (124 mg, 0.2 mmol), bis(2-methylallyl) (1,5-cyclooctadiene)ruthenium (II) (68.7 mg, 0.22 mmol) and tetrafluoroboric acid in Et$_2$O (0.06 mL, 0.4 mmol). The reaction was stirred at 80° C. under a H$_2$ atmosphere (40 atm) for 16 h. Then the reaction was concentrated, washed with saturated aqueous NaHCO$_3$ (20 mL), and extracted with EtOAc (20 mL×3). The combined organic layers were washed with brine (20 mL), dried over anhydrous MgSO$_4$ and filtered. The filtrate was concentrated and purified by column chromatography (SiO$_2$, PE:EtOAc=20:1, v/v) to give the title compound. MS (ESI) m/z: 396 [M+H]$^+$. $^1$H NMR (400 MHz, CDCl$_3$): δ 7.08 (d, J=7.4 Hz, 1H), 6.96 (d, J=7.4 Hz, 1H), 6.88 (s, 1H), 4.56 (br. s., 2H), 3.73 (s, 3H), 3.65 (br. s., 2H), 2.81 (br. s., 3H), 1.89 (t, J=10.2 Hz, 1H), 1.50 (s, 9H), 1.11-1.01 (m, J=4.7 Hz, 1H), 0.94 (d, J=6.7 Hz, 3H), 0.62-0.51 (m, 1H), 0.40-0.20 (m, 2H), 0.03 (m, 1H).

Intermediate 4

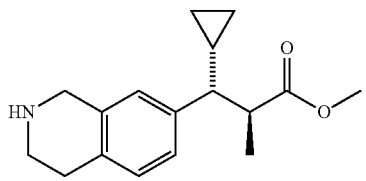 [SMILES: COC(=O)[C@@H](C)[C@H](c1ccc2c(c1)CNCC2)C1CC1]

(2S,3R)-Methyl 3-cyclopropyl-2-methyl-3-(1,2,3,4-tetrahydroisoquinolin-7-yl) propanoate To a solution of intermediate 3 (320 mg, 0.86 mmol) in DCM (3 mL) was added TFA (0.6 mL, 7.8 mmol) at 0° C. The reaction was stirred at rt for 1.5 h, then concentrated, washed with saturated aqueous NaHCO$_3$ (20 mL), and extracted with EtOAc (30 mL×3). The combined organic layers were washed with brine (20 mL) dried over anhydrous MgSO$_4$ and filtered. The filtrate was concentrated to give the title compound. MS (ESI) m/z: 274 [M+H]$^+$.

Intermediate 5

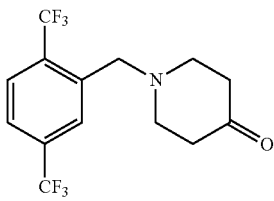 [SMILES: O=C1CCN(Cc2cc(C(F)(F)F)ccc2C(F)(F)F)CC1]

1-(2,5-bis(Trifluoromethyl)benzyl)piperidin-4-one

To a solution of piperidin-4-one (161 mg, 1.6 mmol) in CH$_3$CN (5 mL) was added K$_2$CO$_3$ (675 mg, 4.9 mmol), followed by the addition of 2-(bromomethyl)-1, 4-bis(trifluoromethyl)benzene (500 mg, 1.6 mmol). The reaction was stirred at rt for 16 h. Then the mixture was concentrated, diluted with water (10 mL) and extracted with EtOAc (10 mL×3). The combined organic layers were washed with brine (10 mL), dried over anhydrous Na$_2$SO$_4$, filtered and concentrated in vacuo. The resulting residue was purified by flash column chromatography (SiO$_2$, PE:EtOAc=50:1, v/v) to give the title compound. $^1$H NMR (400 MHz, CDCl$_3$): δ 8.19 (br. s., 1H), 7.79 (d, J=7.9 Hz, 1H), 7.64 (d, J=7.1 Hz, 1H), 3.83 (br. s., 2H), 2.87-2.74 (m, 4H), 2.58-2.43 (m, 4H).

Intermediate 6

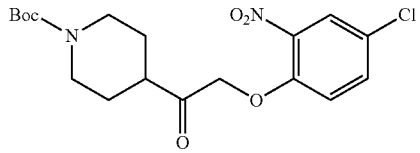 [SMILES: CC(C)(C)OC(=O)N1CCC(C(=O)COc2ccc(Cl)cc2[N+](=O)[O-])CC1]

tert-Butyl 4-(2-(4-chloro-2-nitrophenoxy)acetyl)piperidine-1-carboxylate

A mixture of tert-butyl 4-(2-bromoacetyl) piperidine-1-carboxylate (200 mg, 0.6 mmol), K$_2$CO$_3$ (271 mg, 1.9 mmol) and 4-chloro-2-nitrophenol (170 mg, 0.9 mmol) in acetonitrile (4 mL) was stirred at 20° C. for 14 h. Then the mixture was diluted with water (20 mL), and extracted with EtOAc (30 mL×3). The combined organic layers were washed with brine (40 mL), dried over anhydrous MgSO$_4$ and filtered. The filtrate was concentrated under reduced pressure. The resulting residue was purified by flash column chromatography (PE:EtOAc=10:1, v/v) to give the title compound. MS (ESI) m/z: 299 [M−100+H]$^+$. $^1$H NMR (400 MHz, CDCl$_3$): δ 7.93 (d, J=2.4 Hz, 1H), 7.52 (dd, J=2.5, 8.9 Hz, 1H), 6.91 (d, J=9.0 Hz, 1H), 4.68 (s, 2H), 3.04 (tt, J=3.5, 11.4 Hz, 1H), 2.86 (br. s., 2H), 1.87 (d, J=12.8 Hz, 2H), 1.60-1.49 (m, 4H), 1.45 (s, 9H).

Intermediate 7

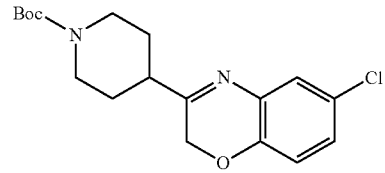 [SMILES: CC(C)(C)OC(=O)N1CCC(C2=Nc3cc(Cl)ccc3OC2)CC1]

tert-Butyl 4-(6-chloro-2H-benzo[b][1,4]oxazin-3-yl)piperidine-1-carboxylate

To a mixture of intermediate 6 (3.00 g, 7.52 mmol) in EtOH (30 mL) and H$_2$O (12 mL) was added iron power (1.26 g, 22.5 mmol) and NH$_4$Cl (4.02 g, 75 mmol). The reaction was stirred at 78° C. for 1.5 h, then concentrated, diluted with EtOAc (50 mL) and filtered. To the filtrate was added water (30 mL), followed by extraction with EtOAc (40 mL×3). The combined organic layers were washed with brine (20 mL), dried over anhydrous MgSO$_4$, filtered and concentrated to give the title compound. MS (ESI) m/z: 295 [M−56+H]$^+$.

Intermediate 8

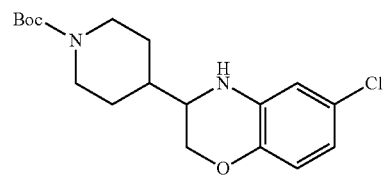 [SMILES: CC(C)(C)OC(=O)N1CCC(C2COc3ccc(Cl)cc3N2)CC1]

tert-Butyl 4-(6-chloro-3,4-dihydro-2H-benzo[b][1,4]oxazin-3-yl)piperidine-1-carboxylate To a mixture of intermediate 7 (2.60 g, 7.41 mmol) in EtOH (20 mL) and H$_2$O (5 mL) was added NaBH$_4$ (0.561 g, 14.8 mmol). The mixture was stirred at 90° C. for 2 h. Then the reaction was concentrated, diluted with H$_2$O (30 mL) and extracted with EtOAc (40 mL×3). The combined organic layers were washed with brine (30 mL), dried over anhydrous MgSO$_4$ and filtered. The filtrate was concentrated and purified by flash column chromatography (SiO$_2$, PE:EtOAc=20:1, v/v) to give the title compound. MS (ESI) m/z: 297 [M−56+H]$^+$. $^1$H NMR (400 MHz, CDCl$_3$): δ 6.68 (d, J=1.0 Hz, 1H), 6.61-6.53 (m, 2H), 4.15 (dd, J=2.3, 10.7 Hz, 2H), 4.10-4.02 (m, 1H), 3.14 (br. s., 1H), 2.67 (br. s., 2H), 1.83-1.60 (m, 4H), 1.46 (s, 9H), 1.34-1.17 (m, 2H).

Intermediate 9

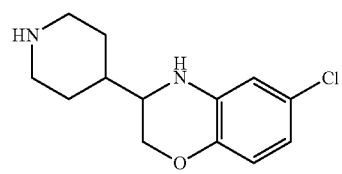 [SMILES: Clc1ccc2c(c1)NC(C1CCNCC1)CO2]

6-Chloro-3-(piperidin-4-yl)-3,4-dihydro-2H-benzo[b][1,4]oxazine

To a solution of intermediate 8 (2.6 g, 7.4 mmol) in DCM (15 mL) was added TFA (4 mL, 52 mmol) at 0° C. The reaction was stirred at 20° C. for 1.5 h, then concentrated and saturated aqueous NaHCO$_3$ (20 mL) and EtOAc (20 mL) were added. The reaction mixture was extracted with EtOAc (20 mL×3). The combined organic layers were washed with brine (20 mL), dried over anhydrous MgSO$_4$, filtered and concentrated to the title compound.

Intermediate 10

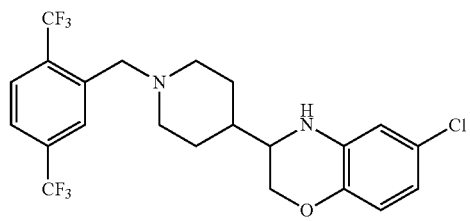 [SMILES: FC(F)(F)c1ccc(C(F)(F)F)c(CN2CCC(C3COc4ccc(Cl)cc4N3)CC2)c1]

3-(1-(2,5-Bis(trifluoromethyl)benzyl)piperidin-4-yl)-6-chloro-3,4-dihydro-2H-benzo[b][1,4]oxazine To a solution of 2,5-bis (trifluoromethyl) benzyl methanesulfonate (2.55 g, 7.91 mmol) and intermediate 9 (2.00 g, 7.91 mmol) in acetonitrile (30 mL) was added K$_2$CO$_3$ (2.18 g, 15.83 mmol). The reaction was stirred at 20° C. for 15 h. Then the reaction was concentrated, diluted with H$_2$O (50 mL) and extracted with EtOAc (40 mL×3). The combined organic layers were washed with brine (50 mL), dried over anhydrous MgSO$_4$ and filtered. The filtrate was concentrated and purified by flash column chromatography (SiO$_2$, PE:EtOAc=5:1, v/v) to give the title compound. MS (ESI) m/z: 479 [M+H]$^+$. $^1$H NMR (400 MHz, CDCl$_3$): δ 1.40-1.54 (m, 3H) 1.70-1.84 (m, 2H) 2.03-2.14 (m, 2H) 2.84-2.95 (m, 2H) 3.19 (t, J=6.27 Hz, 1H) 3.68 (s, 2H) 3.94 (br. s., 1H) 4.05 (dd, J=10.67, 6.15 Hz, 1H) 4.20 (dd, J=10.67, 2.38 Hz, 1H) 6.55-6.61 (m, 2H) 6.65-6.71 (m, 1H) 7.60 (d, J=8.28 Hz, 1H) 7.76 (d, J=8.28 Hz, 1H) 8.14 (s, 1H).

Intermediate 11

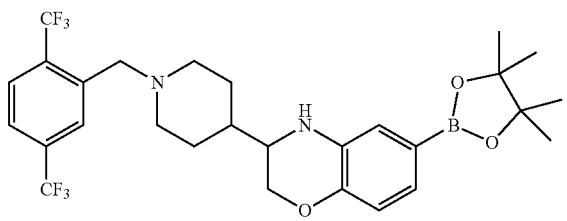 [SMILES: CC1(C)OB(c2ccc3c(c2)NC(C2CCN(Cc4cc(C(F)(F)F)ccc4C(F)(F)F)CC2)CO3)OC1(C)C]

3-(1-(2,5-Bis(trifluoromethyl)benzyl)piperidin-4-yl)-6-(4,4,5,5-tetramethyl-1,3,2-dioxaborolan-2-yl)-3,4-dihydro-2H-benzo[b][1,4]oxazine A mixture of bis-pinacolatodiboron (53 mg, 0.21 mmol), intermediate 10 (50 mg, 0.10 mmol), KOAc (31 mg, 0.31 mmol), dicyclohexyl(2',4',6'-triisopropyl-[1,1'-biphenyl]-2-yl)-phosphine (2.48 mg, 5.2 μmol) and Pd$_2$(dba)$_3$ (47.8 mg, 0.05 mmol) in dioxane (2 mL) was stirred at 110° C. for 18 h. Then the reaction was cooled to rt, and water (25 mL) was added. The aqueous phase was separated and extracted with EtOAc (20 mL×3). The combined organic layers were washed with water (30 mL) and brine (40 mL), dried over anhydrous MgSO$_4$ and filtered. The filtrate was concentrated under reduced pressure. The resulting residue was purified by prep-TLC (SiO$_2$, PE:EtOAc=10:1, v/v) to give the title compound. MS (ESI) m/z: 571 [M+H]$^+$.

Intermediate 12

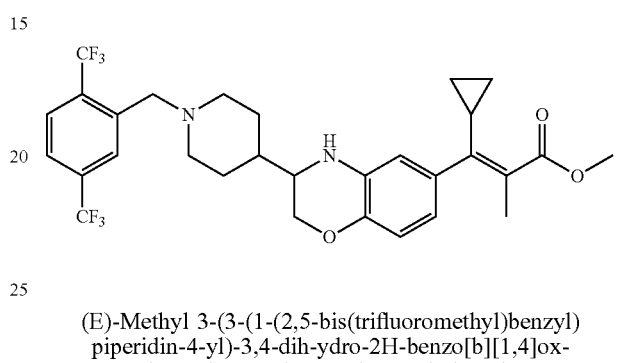

(E)-Methyl 3-(3-(1-(2,5-bis(trifluoromethyl)benzyl)piperidin-4-yl)-3,4-dih-ydro-2H-benzo[b][1,4]oxazin-6-yl)-3-cyclopropyl-2-methylacrylate A mixture of Pd(PPh$_3$)$_2$Cl$_2$ (8.6 mg, 0.01 mmol), K$_2$CO$_3$ (34 mg, 0.24 mmol), (Z)-methyl 3-cyclopropyl-2-methyl-3-(tosyloxy) acrylate (42 mg, 0.13 mmol) and intermediate 11 (70 mg, 0.12 mmol) in THF (2.5 mL) and H$_2$O (0.5 mL) was stirred at 80° C. for 1 h. Then the reaction was cooled to rt and water (35 mL) was added to the mixture. The aqueous phase was extracted with EtOAc (20 mL×3). The combined organic layers were washed with brine (30 mL), dried over anhydrous MgSO$_4$ and filtered. The filtrate was concentrated under reduced pressure. The resulting residue was purified by prep-TLC (PE:EtOAc=10:1, v/v) to give the title compound. MS (ESI) m/z: 583 [M+H]$^+$. $^1$H NMR (400 MHz, CDCl$_3$): δ 8.14 (br. s., 1H), 7.76 (d, J=7.8 Hz, 1H), 7.60 (d, J=7.4 Hz, 1H), 6.66 (d, J=8.2 Hz, 1H), 6.30-6.21 (m, 2H), 4.25 (d, J=10.2 Hz, 1H), 4.08-3.97 (m, 1H), 3.68 (br. s., 2H), 3.41 (s, 3H), 3.19 (br. s., 1H), 2.90 (br. s., 2H), 2.20-2.01 (m, 5H), 1.82-1.71 (m, J=5.1, 8.0, 8.0 Hz, 3H), 1.49 (br. s., 3H), 0.77-0.67 (m, 2H), 0.37 (m, 2H).

Intermediate 13

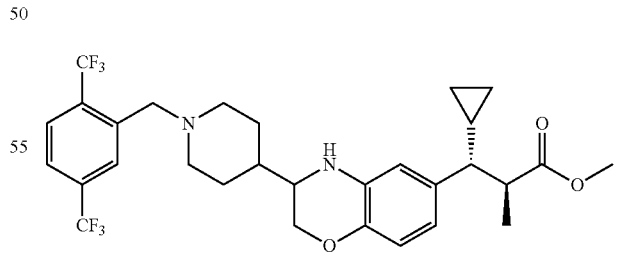

(2S,3R)-Methyl 3-(3-(1-(2,5-bis(trifluoromethyl)benzyl)piperidin-4-yl)-3,4-dihydro-2H-benzo[b][1,4]oxazin-6-yl)-3-cyclopropyl-2-methylpropanoate A mixture of Josiphos (48 mg, 0.09 mmol), tetrafluoroboric acid in Et$_2$O (0.02 mL, 0.15 mmol), bis(2-methylallyl)-(1,5-cyclooctadiene)ruthenium (II) (26.8 mg, 0.084 mmol) and intermediate 12 (287 mg, 0.49 mmol) in DCM (0.3 mL) and MeOH (3 mL) was stirred at 80° C. under H$_2$ (40 atm) for 16 h. Then the reaction was concentrated, diluted with saturated NaHCO$_3$ (10 mL) and extracted with EtOAc (10 mL×3). The combined organic layers were washed with brine (20 mL), dried over anhydrous MgSO$_4$ and filtered. The filtrate was concentrated and purified by prep-TLC (SiO$_2$, PE:EtOAc=10:1, v/v) to give the title compound. MS (ESI) m/z: 585 [M+H]$^+$. $^1$H NMR (400 MHz, CDCl$_3$): δ 8.15 (br. s., 1H), 7.76 (d, J=8.2 Hz, 1H), 7.60 (d, J=7.8 Hz, 1H), 6.71 (d, J=8.2 Hz, 1H), 6.47-6.37 (m, 2H), 4.25 (dd, J=2.2, 10.4 Hz, 1H), 4.01 (dd, J=7.4, 10.2 Hz, 1H), 3.75-3.66 (m, 4H), 3.22 (br. s., 1H), 2.91 (br. s., 2H), 2.79-2.67 (m, 1H), 2.10 (t, J=10.0 Hz, 2H), 1.87-1.71 (m, 3H), 1.63 (d, J=8.2 Hz, 1H), 1.57-1.42 (m, 3H), 1.06-0.98 (m, 1H), 0.94 (d, J=6.7 Hz, 3H), 0.58-0.48 (m, 1H), 0.38-0.28 (m, 1H), 0.26-0.15 (m, 1H), 0.05-0.06 (m, 1H).

Intermediate 14

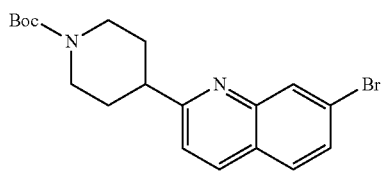 [SMILES: CC(C)(C)OC(=O)N1CCC(c2ccc3ccc(Br)cc3n2)CC1]

tert-Butyl 4-(7-bromoquinolin-2-yl)piperidine-1-carboxylate

To a solution of 2-amino-4-bromobenzaldehyde (704 mg, 3.52 mmol) and tert-butyl 4-acetyl-piperidine-1-carboxylate (800 mg, 3.52 mmol) in EtOH (20 mL) was added sodium 2-methylpropan-2-olate (676 mg, 7.04 mmol). The mixture was stirred at 80° C. for 2 h, then concentrated under reduced pressure. To the resulting residue was added H$_2$O (10 mL) and the resulting mixture was extracted with EtOAc (10 mL×3). The combined organic layers were dried over sodium sulfate, and then filtered. The filtrate was concentrated in vacuo to give the crude product, which was purified by column chromatography (SiO$_2$, PE:ethyl acetate=5:1, v/v) to give the title compound. LC/MS (ESI) m/z: 391.2 [M]+, 393.2 [M+2H]$^+$. $^1$H NMR (400 MHz, CDCl$_3$): δ=8.21 (s, 1H), 8.05 (d, J=8.6 Hz, 1H), 7.66-7.61 (m, 1H), 7.60-7.53 (m, 1H), 7.30 (d, J=8.6 Hz, 1H), 4.27 (br. s., 2H), 3.02 (tt, J=3.6, 11.9 Hz, 1H), 2.88 (br. s., 2H), 2.00-1.92 (m, 2H), 1.88-1.76 (m, 2H), 1.47 (s, 9H).

Intermediate 15

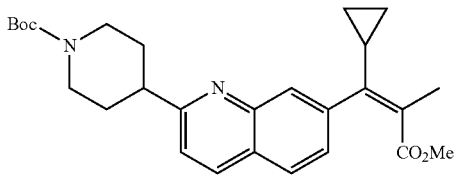 [SMILES: COC(=O)/C(C)=C(\c1ccc2ccc(C3CCN(C(=O)OC(C)(C)C)CC3)nc2c1)C1CC1]

tert-butyl 4-(7-(1-cyclopropyl-3-methoxy-2-methyl-3-oxoprop-1-en-1-yl) quinolin-2-yl)piperidine-1-carboxylate Step A: To a solution of intermediate 14 (400 mg, 1.022 mmol), bis-pinacolato-diboron (277 mg, 1.23 mmol) and KOAc (301 mg, 3.07 mmol) in 1,4-dioxane (10 mL) was added PdCl$_2$(dppf) (74.8 mg, 0.102 mmol). The mixture was stirred at 100° C. for 40 min under N$_2$, then concentrated under reduced pressure. The resulting crude product which was purified by column chromatography (SiO$_2$, PE:ethyl acetate=3:1, v/v) to give tert-butyl-4-(7-(4,4,5-trimethyl-1,3,2-dioxaborolan-2-yl)quinolin-2-yl)-piperidine-1-carboxylate. $^1$H NMR (400 MHz, CDCl$_3$): δ=8.55 (s, 1H), 8.06 (d, J=8.4 Hz, 1H), 7.85-7.79 (m, 1H), 7.76-7.69 (m, 1H), 7.30 (d, J=8.4 Hz, 1H), 4.26 (br. s., 2H), 3.03 (tt, J=3.6, 11.7 Hz, 1H), 2.89 (br. s., 2H), 2.01-1.93 (m, 2H), 1.90-1.77 (m, 2H), 1.47 (s, 9H), 1.36 (s, 12H).

Step B: To a solution of tert-butyl 4-(7-(4,4,5-trimethyl-1,3,2-dioxa borolan-2-yl)-quinolin-2-yl)piperidine-1-carboxylate (200 mg, 0.5 mmol, Step A), (E)-methyl 3-cyclopropyl-2-methyl-3-(tosyloxy)acrylate (170 mg, 0.5 mmol) and K$_2$CO$_3$ (126 mg, 0.9 mmol) in THF (16 mL) and water (4.0 mL) was added Pd(PPh$_3$)$_2$Cl$_2$ (32.0 mg, 0.0456 mmol). The mixture was stirred at 70° C. for 1.5 h under N$_2$. Then water (10 mL) was added and the resulting aqueous layer was extracted with EtOAc (10 mL×3). The combined organic layers were dried over sodium sulfate, and then filtered. The filtrate was concentrated under reduced pressure to give the crude product, which was purified by column chromatography (SiO$_2$, PE:ethyl acetate=3:1, v/v) to give the title compound.

Intermediate 16

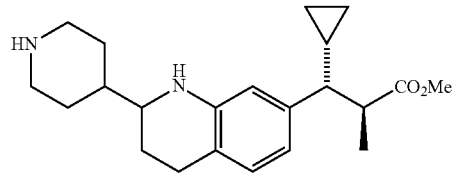 [SMILES: COC(=O)[C@@H](C)[C@H](c1ccc2c(c1)NC(C1CCNCC1)CC2)C1CC1]

(2S,3R)-Methyl 3-cyclopropyl-2-methyl-3-(2-(piperidin-4-yl)-1,2,3,4-tetrahydroquinolin-7-yl)propanoate A solution of intermediate 15 (30.0 mg, 0.06 mmol), Josiphos (21.3 mg, 0.06 mmol), bis(2-methylallyl)(1,5-cyclooctadiene)ruthenium(II) (36.1 mg, 0.06 mmol) and tetrafluoroboric acid (5.9 mg, 0.06 mmol) in MeOH (2.0 mL) and DCM (0.4 mL) was stirred at 80° C. for 20 h under H$_2$ (4 MPa). Then the reaction mixture was filtered and the filtrate was purified by preparative-HPLC (0.1% TFA, v/v) to give the title compound. LCMS (ESI) m/z: 357.3 [M+H]$^+$. $^1$H NMR (400 MHz, Methanol-d4): δ=6.92 (d, J=7.3 Hz, 1H), 6.57-6.46 (m, 2H), 3.73 (s, 3H), 3.48 (d, J=11.8 Hz, 2H), 3.19 (br. s., 1H), 3.00 (t, J=12.8 Hz, 2H), 2.89-2.71 (m, 4H), 1.85-1.33 (m, 7H), 1.10-0.97 (m, 1H), 0.92 (d, J=6.8 Hz, 3H), 0.61-0.48 (m, 1H), 0.34-0.24 (m, 1H), 0.22-0.14 (m, 1H), −0.02 (br. s., 1H).

Intermediate 17

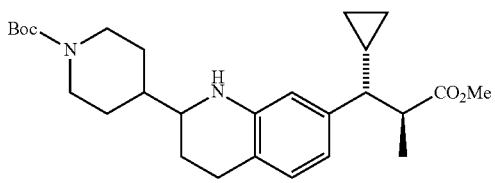 [SMILES: COC(=O)[C@@H](C)[C@H](c1ccc2c(c1)NC(C1CCN(C(=O)OC(C)(C)C)CC1)CC2)C1CC1]

tert-Butyl 4-(7-((1R,2S)-1-cyclopropyl-3-methoxy-2-methyl-3-oxopropyl)-1,2,3,4-tetrahydroquinolin-2-yl)piperidine-1-carboxylate To a solution of intermediate 16 (1.58 g, 4.4 mmol) was added BOC-anhydride (1.03 mL, 4.43 mmol) and Et$_3$N (0.927 mL, 6.65 mmol) in DCM (20 mL). The solution was stirred at 20° C. for 30 min. Then the mixture was concentrated under reduced pressure to give rise to the crude product, which was purified by column chromatography (SiO$_2$, PE:ethyl acetate=3:1, v/v) to give the title compound. LCMS (ESI) m/z: 457.3 [M+H]$^+$ Intermediates 18 and 19

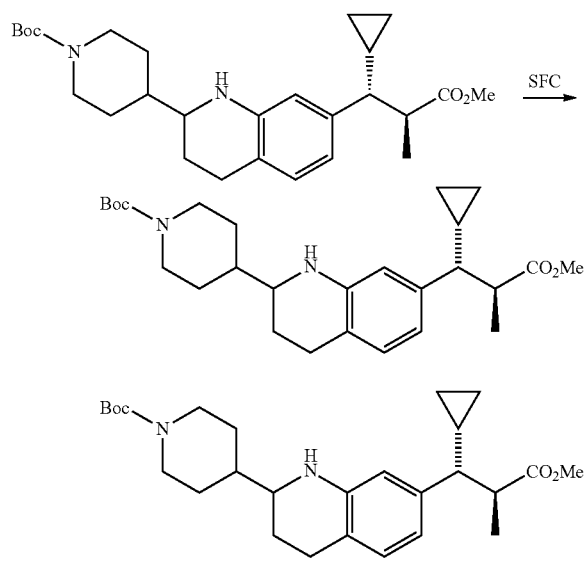

tert-Butyl 4-((R or S)-7-((1R,2S)-1-cyclopropyl-3-methoxy-2-methyl-3-oxopropyl)-1,2,3,4-tetrahydroquinolin-2-yl)piperidine-1-carboxylate and tert-butyl 4-((S or R)-7-((1R,2S)-1-cyclopropyl-3-methoxy-2-methyl-3-oxopropyl)-1,2,3,4-tetrahydroquinolin-2-yl)-piperidine-1-carboxylate Tert-butyl-4-(7-((1R,2S)-1-cyclopropyl-3-methoxy-2-methyl-3-oxopropyl)-1,2,3,4-tetrahydroquinolin-2-yl)-piperidine-1-carboxylate (1.5 g, 3.29 mmol) was separated by SFC (Column: Chiralpak IC-3 150×4.6 mm I.D., 3 um Mobile phase: A: CO$_2$ B:IPA (0.05% DEA) Gradient: from 5% to 40% of B in 5.5 min and hold 40% for 3 min, then 5% of B for 2.5 min; flow rate: 2.5 mL/min; column temperature: 40° C.) to give tert-butyl 4-((R or S)-7-((1R,2S)-1-cyclopropyl-3-methoxy-2-methyl-3-oxopropyl)-1,2,3,4-tetrahydroquinolin-2-yl)piperidine-1-carboxylate (intermediate 18), and tert-butyl 4-((S or R)-7-((1R,2S)-1-cyclopropyl-3-methoxy-2-methyl-3-oxopropyl)-1,2,3,4-tetrahydroquinolin-2-yl)piperidine-1-carboxylate (intermediate 19).

Intermediate 20

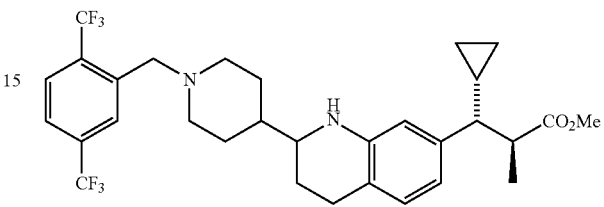

Step A: Intermediate 18 (100 mg, 0.219 mmol) was dissolved in 4N HCl in dioxane (4.0 mL, 16.0 mmol). The mixture was stirred at 20° C. for 1 h, then concentrated under reduced pressure to give (2S,3R)-methyl 3-cyclopropyl-2-methyl-3-((R or S)-2-(piperidin-4-yl)-1,2,3,4-tetrahydroquinolin-7-yl)propanoate. LCMS (ESI) m/z: 357.2 [M+H]$^+$ Step B: To a solution of 2,5-bis(trifluoromethyl)benzyl methanesulfonate (148 mg, 0.46 mmol), (2S,3R)-methyl 3-cyclopropyl-2-methyl-3-((R or S)-2-(piperidin-4-yl)-1,2,3,4-tetrahydroquinolin-7-yl)propanoate (117 mg, 0.33 mmol) in MeCN (5.0 mL), was added K$_2$CO$_3$ (227 mg, 1.6 mmol). The reaction mixture was stirred at 20° C. for 12 h. The reaction mixture was concentrated under reduced pressure. The resulting residue was purified by column chromatography (SiO$_2$, PE:ethyl acetate=10:1-5:1, v/v) to give (2S,3R)-methyl 3-((R or S)-2-(1-(2,5-bis(trifluoromethyl)benzyl)-piperidin-4-yl)-1,2,3,4-tetrahydroquinolin-7-yl)-3-cyclopropyl-2-methylpropanoate. LC/MS (ESI) m/z: 583.3 [M+H]$^+$ $^1$H NMR (400 MHz, Methanol-d$_4$): δ8.18 (s, 1H), 7.86 (d, J=8.2 Hz, 1H), 7.72 (d, J=8.2 Hz, 1H), 6.79 (d, J=7.4 Hz, 1H), 6.38 (s, 1H), 6.32 (d, J=7.4 Hz, 1H), 3.71 (br. s., 2H), 3.68 (s, 3H), 3.03 (s, 1H), 2.90-2.75 (m, 2H), 2.81-2.64 (m, 3H), 2.14-2.05 (m, 2H), 1.96-1.77 (m, 3H), 1.72-1.64 (m, 2H), 1.43 (br. s., 3H), 1.01-0.94 (m, 1H), 0.88 (d, J=7.0 Hz, 3H), 0.53-0.42 (m, 1H), 0.31-0.20 (m, 1H), 0.12 (dd, J=4.7, 9.4 Hz, 1H), −0.05 (td, J=4.8, 9.5 Hz, 1H).

Intermediate 21

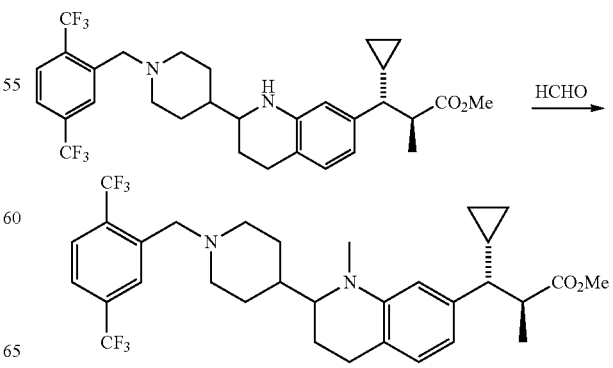

(2S,3R)-methyl 3-((R or S)-2-(1-(2,5-bis(trifluoromethyl)benzyl)piperidin-4-yl)-1-methyl-1,2,3,4-tetrahydroquinolin-7-yl)-3-cyclopropyl-2-methylpropanoate To a solution of intermediate 20 (180 mg, 0.31 mmol) in MeOH (10 mL) was added paraformaldehyde (400 mg, 0.31 mmol), H₂O (100 µl, 5.5 mmol), and AcOH (100 µl, 1.7 mmol). The mixture was stirred at 20° C. for 10 min, then NaCNBH₄ (194 mg, 3.1 mmol) was added. The reaction mixture was stirred at 20° C. for 12 h, then H₂O (3.0 mL) was added. The aqueous phase was extracted with EtOAc (10 mL×3). The combined organic layers were dried over sodium sulfate, then filtered. The filtrate was concentrated under reduced pressure to give the crude product, which was purified by prep-TLC (SiO₂, PE:ethyl acetate=10:1, v/v) to give the title compound. LCMS (ESI) m/z: 597.4 [M+H]⁺

Intermediate 22

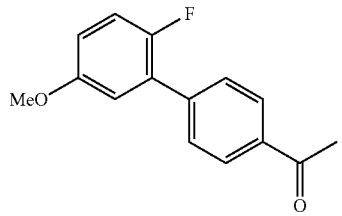 [SMILES: COc1ccc(F)c(-c2ccc(C(C)=O)cc2)c1]

1-(2'-Fluoro-5'-methoxy-[1,1'-biphenyl]-4-yl)ethanone

To a solution of 1-(4-bromophenyl)ethanone (15.0 g, 75.0 mmol) in 1,4-dioxane (150 mL) and water (30 mL) was added (2-fluoro-5-methoxyphenyl)boronic acid (13.5 g, 79 mmol), K₃PO₄ (40.0 g, 188 mmol) and PdCl₂(dppf) (2.76 g, 3.77 mmol) at rt. The mixture was degassed and refilled with N₂ for several times. Then the reaction mixture was heated to 80° C. for 8 h. The mixture was then concentrated and poured into water (50 mL). EtOAc (50 mL) was added, and the resulting organic layer was separated. The aqueous layer was extracted with EtOAc (50 mL×3). The combined organic layers were dried over Na₂SO₄, filtered and concentrated under reduced pressure. The resulting crude product was purified by column chromatography (silica gel, PE:EtOAc=10:1-1:1, v/v) to give the title compound. ¹H NMR (400 MHz, CDCl₃): δ=8.04 (d, J=8.4 Hz, 2H), 7.65 (d, J=7.1 Hz, 2H), 7.10 (t, J=9.5 Hz, 1H), 6.96 (dd, J₁=3.0, J₂=6.1 Hz, 1H), 6.88 (td, J=3.4, 8.8 Hz, 3H), 3.84 (s, 3H), 2.65 (s, 3H).
MS (ESI) m/z: 245.1 [M+H]⁺.

Intermediate 23

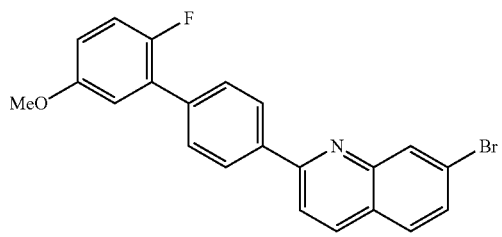 [SMILES: COc1ccc(F)c(-c2ccc(-c3ccc4ccc(Br)cc4n3)cc2)c1]

7-Bromo-2-(2'-fluoro-5'-methoxy-[1,1'-biphenyl]-4-yl)quinoline

To a solution of 2-amino-4-bromobenzaldehyde (4.09 g, 20.47 mmol) and 1-(2'-fluoro-5'-methoxy-[1,1'-biphenyl]-4-yl)ethanone (5.00 g, 20.5 mmol) in EtOH (60 mL) was added KOH (2.53 g, 45.0 mmol) and molecular sieves (1.00 g) at rt. The mixture was heated to 90° C. for 2 h, then filtered and concentrated to afford the crude product, which was purified by column chromatography (silica gel, PE to PE:EtOAc=10:1, v/v) to give the title compound. ¹H NMR (400 MHz, CDCl₃): δ=8.43 (s, 1H), 8.32-8.24 (m, 3H), 7.99 (d, J=8.5 Hz, 1H), 7.80-7.73 (m, 3H), 7.69-7.64 (m, 1H), 7.16 (t, J=9.5 Hz, 1H), 7.06 (dd, J₁=3.3, J₂=6.3 Hz, 1H), 6.91 (td, J=3.5, 9.0 Hz, 1H), 3.90 (s, 3H). MS (ESI) m/z: 408.0/410.0 [M+H]⁺.

Intermediate 24

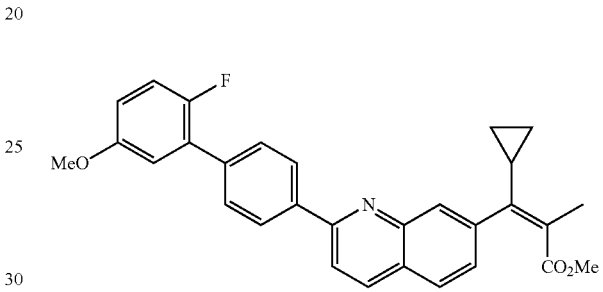

(Z)-Methyl 3-cyclopropyl-3-(2-(2'-fluoro-5'-methoxy-[1,1'-biphenyl]-4-yl)quinolin-7-yl)-2-methylacrylate Step A: To a solution of intermediate 23 (4 g, 9.80 mmol) and bis-pinacolatodiboron (2.99 g, 11.8 mmol) in 1,4-dioxane (50 mL) was added KOAc (2.88 g, 29.4 mmol), and PdCl₂(dppf) (0.717 g, 0.98 mmol) at rt. The mixture was degassed and refilled with N₂ for several times. The mixture was heated to 70° C. for 1.5 h, then filtered and concentrated under reduced pressure to give 2-(2'-fluoro-5'-methoxy-[1,1'-biphenyl]-4-yl)-7-(4,4,5,5-tetramethyl-1,3,2-dioxaborolan-2-yl)quinoline. MS (ESI) m/z: 456.2 [M+H]⁺.

Step B: To a solution of 2-(2'-fluoro-5'-methoxy-[1,1'-biphenyl]-4-yl)-7-(4,4,5,5-tetramethyl-1,3,2-dioxaborolan-2-yl)quinoline (4.00 g, 8.79 mmol) and (E)-methyl 3-cyclopropyl-2-methyl-3-(tosyloxy)acrylate (3.27 g, 10.5 mmol) in THF (50 mL) and water (10 mL) was added K₂CO₃ (3.04 g, 21.9 mmol) and Pd(PPh₃)₂Cl₂ (0.62 g, 0.88 mmol) at rt. The mixture was degassed and refilled with N₂ several times. The reaction mixture was heated to 70° C. for 1.5 h, then water (50 mL) was added, followed by EtOAc (50 mL). The aqueous layer was separated and extracted with ethyl acetate (50 mL×3). The combined organic layers were dried over anhydrous sodium sulfate, filtered and concentrated under reduced pressure. The resulting crude product was purified by column chromatography (silica gel, PE to PE:EtOAc=30:1, v/v) to afford (Z)-methyl 3-cyclopropyl-3-(2-(2'-fluoro-5'-methoxy-[1,1'-biphenyl]-4-yl)quinolin-7-yl)-2-methylacrylate. ¹H NMR (400 MHz, CDCl₃): δ=8.27-8.19 (m, 3H), 7.91 (d, J=8.6 Hz, 1H), 7.79-7.69 (m, 4H), 7.24 (d, J=8.2 Hz, 1H), 7.11 (t, J=9.5 Hz, 1H), 7.03 (dd, J₁=3.1, J₂=6.2 Hz, 1H), 6.90-6.84 (m, 1H), 3.86 (s, 3H), 3.34 (s, 3H), 2.24 (s, 3H), 2.03-1.94 (m, 1H), 0.85-0.77 (m, 2H), 0.44-0.37 (m, 2H).

Intermediate 25

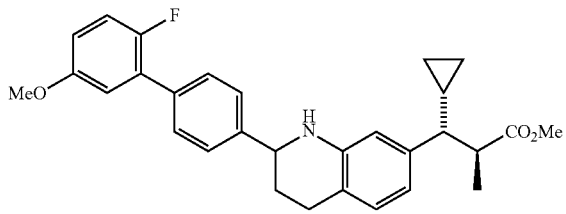

(2S3R)-Methyl 3-cyclopropyl-3-(2-(2'-fluoro-5'-methoxy-[11'-biphenyl]-4-yl)-1,2,3,4-tetrahydroquinolin-7-yl)-2-methylpropanoate To a solution of (E)-methyl-3-cyclopropyl-3-(2-(2'-fluoro-5'-methoxy-[1,1'-biphenyl]-4-yl)quinolin-7-yl)-2-methylacrylate (2.00 g, 4.28 mmol) in MeOH (18 mL) and DCM (2 mL) was added Josiphos (0.232 g, 0.428 mmol), bis(2-methylallyl)(1,5-cyclooctadiene) ruthenium(II) (0.137 g, 0.428 mmol) and tetrafluoroboric acid-diethyl ether complex (0.277 g, 0.856 mmol) at rt. The mixture was stirred at 80° C. for 48 h under 4 Mpa pressure of hydrogen in an autoclave. Then the mixture was concentrated under reduced pressure and the resulting residue was purified by column chromatography (silica gel, PE to PE:EtOAc=10:1, v/v) to give the title compound. MS (ESI) m/z: 474.6 [M+H]$^+$.

Intermediate 26

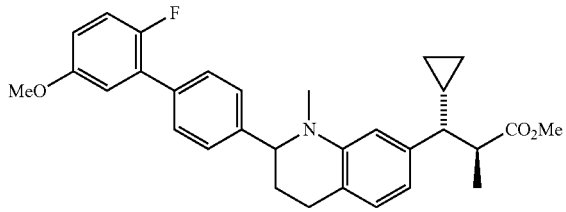 [SMILES: COC(=O)[C@@H](C)[C@H](c1ccc2c(c1)N(C)C(c1ccc(-c3cc(OC)ccc3F)cc1)CC2)C1CC1]

(2S,3R)-Methyl 3-cyclopropyl-3-((RS)-2-(2'-fluoro-5'-methoxy-[1,1'-biphenyl]-4-yl)-1-methyl-1,2,3,4-tetrahydroquinolin-7-yl)-2-methylpropanoate To a solution of Intermediate 25 (300 mg, 0.633 mmol) in DMF (3 mL) was added NaH (50.7 mg, 1.27 mmol) at rt. The mixture was stirred at rt for 10 min. Then iodomethane (450 mg, 3.17 mmol) was added, and the mixture was stirred at rt for 10 h. Then the mixture was diluted with water (10 mL) and EtOAc (10 mL). The aqueous layer was separated and extracted with ethyl acetate (10 mL×3). The combined organic layers were dried over anhydrous sodium sulfate, filtered and concentrated under reduced pressure. The resulting crude product was purified by column chromatography (silica gel, PE to PE:EA=10:1, v/v) to give the title compound. $^1$H NMR (400 MHz, CDCl$_3$): δ=7.50 (d, J=7.0 Hz, 2H), 7.24 (s, 2H), 7.07 (t, J=9.6 Hz, 1H), 6.97-6.90 (m, 2H), 6.82 (td, J=3.2, 8.8 Hz, 1H), 6.49-6.42 (m, 2H), 4.52 (t, J=4.3 Hz, 1H), 3.83 (s, 3H), 3.75 (s, 3H), 2.89 (s, 3H), 2.88-2.81 (m, 1H), 2.65-2.57 (m, 2H), 2.28-2.17 (m, 1H), 2.09-2.00 (m, 1H), 1.87 (t, J=10.0 Hz, 1H), 1.16-1.06 (m, 1H), 1.02 (d, J=6.7 Hz, 3H), 0.61-0.51 (m, 1H), 0.44-0.33 (m, 1H), 0.30-0.21 (m, 1H), 0.11 (br. s., 1H).

Intermediate 27

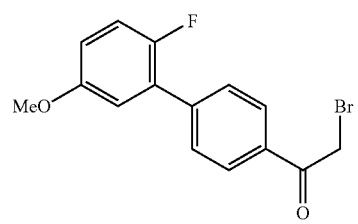 [SMILES: COc1ccc(F)c(-c2ccc(C(=O)CBr)cc2)c1]

2-Bromo-1-(2'-fluoro-5'-methoxy-[1,1'-biphenyl]-4-yl)ethan-1-one

To a solution of intermediate 22 (10.0 g, 40.9 mmol) in DCM (180 mL) was added bromine (2.00 mL, 38.9 mmol) in DCM (30 mL) at 0° C. The reaction mixture was stirred at 0° C. for 1 h, then the mixture was poured into saturated sodium thiosulfate solution (150 mL). The aqueous layer was separated and extracted with DCM (100 mL×2). The combined organic layers were dried over MgSO$_4$, filtered and concentrated under reduced pressure to give the title compound.

Intermediate 28

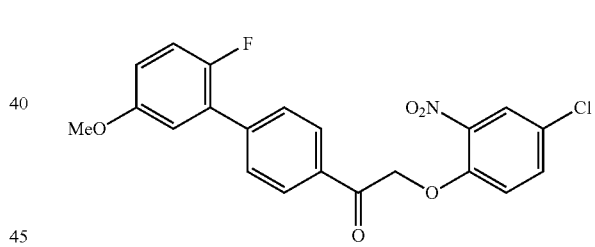

2-(4-Chloro-2-nitrophenoxy)-1-(2'-fluoro-5'-methoxy[1,1'-biphenyl]-4-yl)ethanone To a solution of intermediate 27 (11.8 g, 23.4 mmol) in DMF (120 mL) was added 4-chloro-2-nitrophenol (4.87 g, 28.0 mmol) and K$_2$CO$_3$ (9.69 g, 70.1 mmol). The reaction mixture was stirred at rt for 30 min, then diluted with water (200 mL) and EtOAc (100 mL). The organic layer was separated and the aqueous layer was extracted with EtOAc (100 mL×3). The combined organic layers were washed with brine, dried over anhydrous sodium sulfate, filtered and concentrated under reduced pressure. The resulting crude product was purified by column chromatography (silica gel, EtOAc, DCM) to give the title compound. $^1$H NMR (400 MHz, CDCl$_3$): δ=8.05 (d, J=8.4 Hz, 1H), 7.88 (d, J=2.4 Hz, 1H), 7.69 (d, J=7.3 Hz, 2H), 7.44 (dd, J$_1$=2.4, J$_2$=8.8 Hz, 1H), 7.11 (t, J=9.5 Hz, 1H), 6.97-6.86 (m, 3H), 5.47 (s, 2H), 3.84 (s, 3H). MS (ESI) m/z: 415.9 [M+H]$^+$.

Intermediate 29

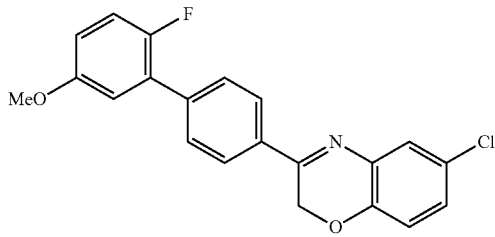 [SMILES: COc1ccc(F)c(-c2ccc(C3=Nc4cc(Cl)ccc4OC3)cc2)c1]

6-Chloro-3-(2'-fluoro-5'-methoxy-[1,1'-biphenyl]-4-yl)-2H-benzo[b][1,4]oxazine

To a solution of intermediate 28 (4.00 g, 9.62 mmol) in EtOH (40 mL) and H$_2$O (10 mL) was added Fe powder (2.15 g, 38.5 mmol) and NH$_4$Cl (4.12 g, 77 mmol) at rt. The mixture was stirred at 90° C. for 2.5 h, then filtered and diluted with H$_2$O (50 mL) and dichloromethane (50 mL). The organic layer was separated. The aqueous layer was extracted with dichloromethane (30 mL×3). The combined organic layers were dried over anhydrous MgSO$_4$, filtered and concentrated under reduced pressure to give the title compound. MS (ESI) m/z: 368.1 [M+H]$^+$.

Intermediate 30

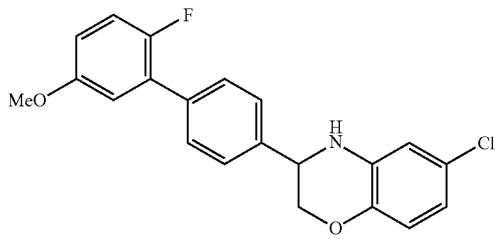 [SMILES: COc1ccc(F)c(-c2ccc(C3COc4ccc(Cl)cc4N3)cc2)c1]

6-Chloro-3-(2'-fluoro-5'-methoxy-[1,1'-biphenyl]-4-yl)-3,4-dihydro-2H-benzo[b][1,4]-oxazine To a solution of 6-chloro-3-(2'-fluoro-5'-methoxy-[1,1'-biphenyl]-4-yl)-2H-benzo[b][1,4]oxazine (3.10 g, 6.74 mmol) in EtOH (40 mL) was added NaBH$_4$ (0.765 g, 20.2 mmol) at rt. The mixture was stirred at 50° C. for 1 h, then diluted with water (100 mL) and EtOAc (50 mL). The organic layer was removed. The aqueous layer was extracted with EtOAc (50 mL×3). The combined organic layers were dried over anhydrous sodium sulfate, filtered and concentrated under reduced pressure to afford the crude product, which was purified by column chromatography (silica gel, PE to PE:EtOAc=10:1, v/v) to give the title compound. $^1$H NMR (400 MHz, CDCl$_3$): δ=7.57 (d, J=7.1 Hz, 1H), 7.45 (d, J=8.2 Hz, 1H), 7.08 (t, J=9.4 Hz, 1H), 6.93 (dd, J$_1$=3.0, J$_2$=6.1 Hz, 1H), 6.84 (td, J=3.4, 8.8 Hz, 1H), 6.77 (d, J=8.4 Hz, 1H), 6.68-6.62 (m, 2H), 4.56 (d, J=6.0 Hz, 1H), 4.32 (d, J=10.8 Hz, 1H), 4.11 (br. s., 1H), 4.01 (dd, J$_1$=8.4, J$_2$=10.6 Hz, 1H), 3.83 (s, 3H). MS (ESI) m/z: 370.1 [M+H]$^+$.

Intermediate 31

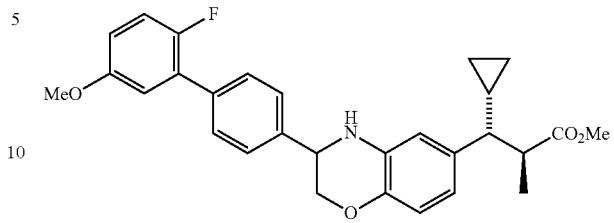

(2S,3R)-Methyl 3-cyclopropyl-3-((R and S)-3-(2'-fluoro-5'-methoxy-[1,1'-bi-phenyl]-4-yl)-3,4-di-hydro-2H-benzo[b][1,4]oxazin-6-yl)-2-methylpropanoate Step A: To a solution of intermediate 30 (1.20 g, 3.24 mmol) and bis-pinacolatodiboron (0.989 g, 3.89 mmol) in dioxane (15 mL) was added dicyclohexyl(2',4',6'-triisopropyl-[1,1'-biphenyl]-2-yl)phosphine (0.155 g, 0.324 mmol), tris(dibenzylideneacetone) dipalladium(0) (0.297 g, 0.324 mmol) and KOAc (0.955 g, 9.73 mmol) at rt. The reaction mixture was degassed and refilled with N$_2$ three times. The reaction mixture was heated to 105° C. for 8 h. Then the mixture was diluted with H$_2$O (50 mL) and EtOAc (30 mL). The organic layer was separated. The aqueous layer was extracted with EtOAc (30 mL×3). The combined organic layers were dried over anhydrous sodium sulfate, filtered and concentrated under reduced pressure to afford the crude product, which was purified by column chromatography (silica gel, PE to PE:EtOAc=10:1, v/v) to give 3-(2'-fluoro-5'-methoxy-[1,1'-biphenyl]-4-yl)-6-(4,4,5,5-tetramethyl-1,3,2-dioxaborolan-2-yl)-3,4-dihydro-2H-benzo[b][1,4]oxazine.

Step B: To a solution of 3-(2'-fluoro-5'-methoxy-[1,1'-biphenyl]-4-yl)-6-(4,4,5,5-tetramethyl-1,3,2-dioxaborolan-2-yl)-3,4-dihydro-2H-benzo[b][1,4]oxazine (1.50 g, 3.25 mmol) and (E)-methyl 3-cyclopropyl-2-methyl-3-(tosyloxy)acrylate (1.211 g, 3.90 mmol) in THF (30 mL) and water (6 mL) was added K$_2$CO$_3$ (1.35 g, 9.75 mmol), and bis(triphenylphosphine)palladium (II) dichloride (0.228 g, 0.325 mmol) at rt. The mixture was degassed and refilled with N$_2$ three times. The mixture was stirred at 75° C. for 4 h. Then the mixture was treated with water (50 mL) and ethyl acetate (30 mL). The organic layer was separated. The aqueous layer was extracted with ethyl acetate (30 mL×3). The combined organic layers were dried over anhydrous sodium sulfate, filtered and concentrated under reduced pressure to afford crude product, which was purified by column chromatography (silica gel, PE:EtOAc=10:1, v/v) to give (E)-methyl 3-cyclopropyl-3-(3-(2'-fluoro-5'-methoxy-[1,1'-biphenyl]-4-yl)-3,4-dihydro-2H-benzo[b][1,4]oxazin-6-yl)-2-methylacrylate. $^1$H NMR (400 MHz, CDCl$_3$): δ=7.60-7.54 (m, 2H), 7.48 (d, J=8.2 Hz, 2H), 7.09 (t, J=9.5 Hz, 1H), 6.94 (dd, J$_1$=3.0, J$_2$=6.1 Hz, 1H), 6.88-6.82 (m, 1H), 6.74 (d, J=8.4 Hz, 1H), 6.36-6.30 (m, 2H), 4.56 (d, J=6.6 Hz, 1H), 4.32 (d, J=10.6 Hz, 1H), 4.09-4.02 (m, 1H), 3.96 (s, 1H), 3.84 (s, 3H), 3.46 (s, 3H), 2.13 (s, 3H), 1.86-1.77 (m, 1H), 0.76 (dd, J$_1$=1.8, J$_2$=8.4 Hz, 2H), 0.41 (dd, J$_1$=5.2, J$_2$=9.6 Hz, 2H).

Step C: To a solution of (Z)-methyl 3-cyclopropyl-3-(3-(2'-fluoro-5'-methoxy-[1,1'-biphenyl]-4-yl)-3,4-dihydro-2H-benzo[b][1,4]oxazin-6-yl)-2-methylacrylate (800 mg, 1.69 mmol) in MeOH (8 mL) and DCM (1 mL) was added Josiphos (92.0 mg, 0.169 mmol), bis(2-methylallyl)(1,5-cyclooctadiene)ruthenium(II) (54.0 mg, 0.169 mmol) and tetrafluoroboric acid-diethyl ether complex (109 mg, 0.338 mmol) at rt. The mixture was stirred at 80° C. for 48 h under 4 MPa in an autoclave. Then the mixture was concentrated under reduced pressure and purified by column chromatography (silica gel, PE to PE:EtOAc=10:1, v/v) to give methyl-3-cyclo-propyl-3-(3-(2'-fluoro-5'-methoxy-[1,1'-biphenyl]-4-yl)-3,4-dihydro-2H-benzo-[b][1,4]oxazin-6-yl)-2-methylpropanoate. $^1$H NMR (400 MHz, CDCl$_3$): δ=7.61-7.55 (m, 2H), 7.52-7.47 (m, 2H), 7.09 (t, J=9.4 Hz, 1H), 6.95 (dd, J$_1$=3.1, J$_2$=6.3 Hz, 1H), 6.88-6.77 (m, 2H), 6.53-6.47 (m, 2H), 4.58 (dd, J$_1$=2.3, J$_2$=8.6 Hz, 1H), 4.32 (dd, J$_1$=2.5, J$_2$=10.8 Hz, 1H), 4.08-3.99 (m, 2H), 3.84 (s, 3H), 3.73 (s, 3H), 2.77 (td, J=2.7, 6.8, 10.0 Hz, 1H), 1.80 (t, J=10.2 Hz, 1H), 1.03 (d, J=4.3 Hz, 1H), 0.98 (d, J=6.7 Hz, 3H), 0.59-0.50 (m, 1H), 0.36 (dd, J$_1$=4.3, J$_2$=8.2 Hz, 1H), 0.23 (dd, J$_1$=4.7, J$_2$=9.0 Hz, 1H), 0.04 (td, J=4.7, 9.4 Hz, 1H). MS (ESI) m/z: 476.3 [M+H]$^+$.

Intermediate 32

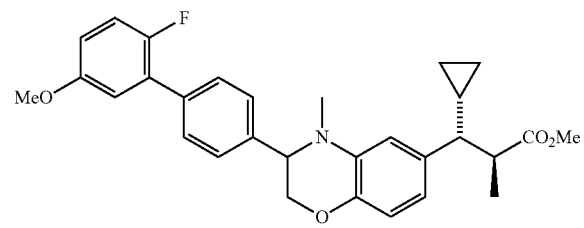 [SMILES: COC(=O)[C@@H](C)[C@H](c1ccc2c(c1)N(C)C(c1ccc(-c3cc(OC)ccc3F)cc1)CO2)C1CC1]

(2S,3R)-Methyl 3-cyclopropyl-3-((RS)-2-(2'-fluoro-5'-methoxy-[1,1'-biphenyl]-4-yl)-1-methyl-1,2,3,4-tetrahydroquinolin-7-yl)-2-methylpropanoate To a solution of intermediate 31 (200 mg, 0.421 mmol) in MeOH (5 mL) and water (0.5 mL) was added NaCNBH$_4$ (159 mg, 2.52 mmol), formaldehyde (101 mg, 3.36 mmol), AcOH (0.1 mL) at rt. The mixture was stirred at rt for 15 h, then diluted with water (5 mL) and EtOAc (5 mL). The organic layer was separated. The aqueous layer was extracted with EtOAc (5 mL×3). The combined organic layers were dried over anhydrous sodium sulfate, filtered and concentrated under reduced pressure. The resulting crude product was purified by preparative-TLC (petroleum ether:ethyl acetate=5:1, v/v) to afford the title compound. $^1$H NMR (400 MHz, CDCl$_3$): δ=7.55 (d, J=7.3 Hz, 2H), 7.36 (d, J=7.9 Hz, 2H), 7.08 (t, J=9.4 Hz, 1H), 6.95 (dd, J$_1$=3.1, J$_2$=6.2 Hz, 1H), 6.87-6.81 (m, 1H), 6.77 (d, J=7.9 Hz, 1H), 6.58 (s, 1H), 6.49 (d, J=7.9 Hz, 1H), 4.36 (d, J=3.5 Hz, 1H), 4.32-4.26 (m, 1H), 4.19-4.14 (m, 1H), 3.87-3.81 (m, 4H), 3.74 (s, 3H), 2.81 (s, 4H), 1.90-1.82 (m, 1H), 1.00 (d, J=6.6 Hz, 3H), 0.61-0.51 (m, 1H), 0.38 (d, J=4.4 Hz, 1H), 0.28-0.21 (m, 1H), 0.11-0.03 (m, 1H). MS (ESI) m/z: 490.1 [M+H]$^+$.

Intermediates 33 and 34

(2S,3R)-Methyl 3-((R or S)-3-(1-(2,5-bis(trifluoromethyl)benzyl)piperidin-4-yl)-3,4-dihydro-2H-benzo[b][1,4]oxazin-6-yl)-3-cyclopropyl-2-methylpropanoate

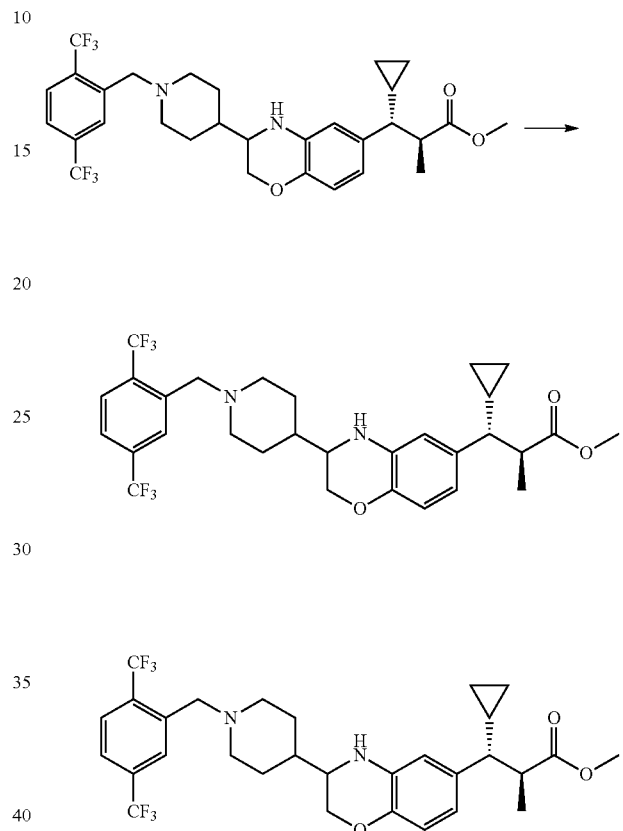

Step A: (2S,3R)-methyl 3-((R or S)-3-(1-(2,5-bis(trifluoromethyl)benzyl)piperidin-4-yl)-3,4-dihydro-2H-benzo[b][1,4]oxazin-6-yl)-3-cyclopropyl-2-methylpropanoate, and (2S,3R)-methyl 3-((S or R)-3-(1-(2,5-bis(trifluoromethyl)benzyl)piperidin-4-yl)-3,4-dihydro-2H-benzo[b][1,4]oxazin-6-yl)-3-cyclopropyl-2-methylpropanoate Intermediate 13 (1.1 g, 1.88 mmol) was separated by SFC (Column: Chiralpak AD-3 150×4.6 mm I.D., 3 um Mobile phase: A: CO$_2$ B: MeOH (0.05% DEA); Gradient: from 5% to 40% of B in 5 min and hold 40% for 2.5 min, then 5% of B for 2.5 min Flow rate: 2.5 mL/min Column temp.: 35° C.; Wavelength: 220 nm) to give (2S,3R)-methyl-3-(3-(1-(2,5-bis(trifluoromethyl)benzyl)-piperidin-4-yl)-3,4-dihydro-2H-benzo[b][1,4]oxazin-6-yl)-3-cyclopropyl-2-methylpropanoate (intermediate 33), and (2S,3R)-methyl-3-(3-(1-(2,5-bis(trifluoromethyl)benzyl)-piperidin-4-yl)-3,4-dihydro-2H-benzo[b][1,4]oxazin-6-yl)-3-cyclopropyl-2methylpropanoate (intermediate 34) MS (ESI) m/z: 585 [M+H]$^+$.

Example 1

(2S,3R)-3-(2-(1-(2,5-bis(Trifluoromethyl)benzyl) piperidin-4-yl)-1,2,34-tetrahydroisoquinolin-7-yl)-3-cyclopropyl-2-methylpropanoic acid

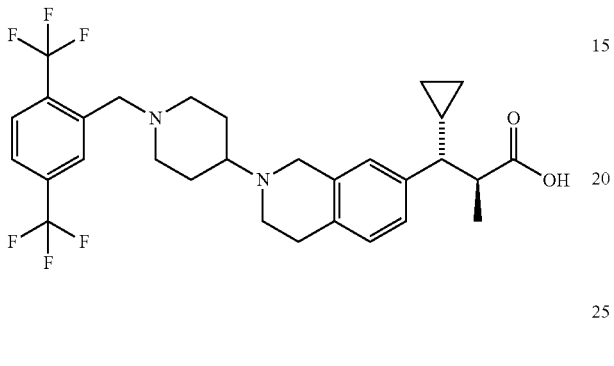

Step A: A mixture of intermediate 4 (22.0 mg, 0.080 mmol) and intermediate 5 (29 mg, 0.09 mmol) in DCM (2 mL) was added sodium triacetoxyborohydride (25.6 mg, 0.121 mmol). The reaction was stirred at 20° C. for 16 h. Then the mixture was diluted with water (30 mL) and extracted with EtOAc (20 mL×3). The combined organic layers were washed with brine (30 mL), dried over anhydrous MgSO$_4$ and filtered. The filtrate was concentrated in vacuo. The resulting residue was purified by prep-TLC (SiO$_2$, PE:EtOAc=5:1, v/v) to give (2S,3R)-methyl 3-(2-(1-(2,5-bis-(trifluoromethyl)-benzyl)piperidin-4-yl)-1,2,3,4-tetrahydroisoquinolin-7-yl)-3-cyclopropyl-2-methylpropanoate. LC/MS (ESI) m/z: 583 [M+H]$^+$.

Step B: To a solution of (2S,3R)-methyl-3-(2-(1-(2,5-bis (trifluoromethyl)benzyl)-piperidin-4-yl)-1,2,3,4-tetrahydroisoquinolin-7-yl)-3-cyclopropyl-2-methylpropanoate (240 mg, 0.40 mmol) in MeOH (1.5 mL), THF (1.5 mL) and H$_2$O (1.5 mL) was added LiOH (493 mg, 20.6 mmol). The reaction was stirred at 52° C. for 20 h. Then the reaction was diluted with water (20 mL) and treated with saturated citric acid to adjust the pH to pH=5. The reaction mixture was extracted with EtOAc (20 mL×3). The combined organic layers were washed with brine (40 mL), dried over anhydrous MgSO$_4$ and filtered. The filtrate was concentrated under reduced pressure. The resulting residue was purified by prep-HPLC (neutral) to give (2S,3R)-3-(2-(1-(2,5-bis (trifluoromethyl)benzyl)piperidin-4-yl)-1,2,3,4-tetra-hydro-isoquinolin-7-yl)-3-cyclopropyl-2-methylpropanoic acid. LC/MS (ESI) m/z: 569 [M+H]$^+$. $^1$H NMR (400 MHz, Methanol-d$_4$): δ 8.29 (s, 1H), 8.01 (d, J=8.2 Hz, 1H), 7.86 (d, J=8.2 Hz, 1H), 7.23 (d, J=1.0 Hz, 1H), 7.17 (d, J=1.0 Hz, 1H), 7.10 (s, 1H), 4.27 (s, 2H), 3.88 (s, 2H), 3.41-3.35 (m, 2H), 3.24-3.02 (m, 5H), 2.87-2.72 (m, 1H), 2.33 (t, J=11.5 Hz, 2H), 2.22 (d, J=11.7 Hz, 2H), 2.06 (t, J=9.8 Hz, 1H), 2.00-1.87 (m, 2H), 1.25-1.15 (m, 1H), 0.94 (d, J=6.8 Hz, 3H), 0.72-0.63 (m, 1H), 0.52-0.44 (m, 1H), 0.38-0.29 (m, 1H), 0.05 (m, 1H).

Example 2

Sodium (2S,3S)-3-((R or S)-3-(1-(2,5-Bis(trifluoromethyl)-benzyl)piperidin-4-yl)-3,4-dihydro-2H-benzo[b][1,4]oxazin-6-yl)-3-cyclopropyl-2-methyl propanoate

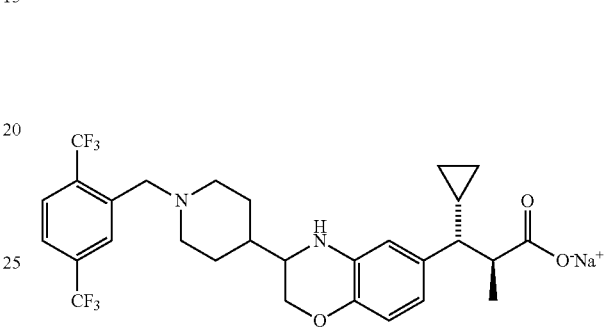

Step A: To a solution of intermediate 33 (80 mg, 0.137 mmol) in MeOH (1 mL), THF (1 mL) and H$_2$O (1 mL) was added LiOH (65.5 mg, 2.74 mmol). The reaction was stirred at 52° C. for 20 h. Then the reaction mixture was acidified with saturated citric acid to adjust the pH to pH=5. The reaction mixture was extracted with EtOAc (20 mL×3). The combined organic layers were washed with brine (40 mL), dried over anhydrous MgSO$_4$ and filtered. The filtrate was concentrated under reduced pressure. The resulting residue was purified by prep-HPLC to give (2S,3R)-methyl 3-((R or S)-3-(1-(2,5-bis(trifluoromethyl)-benzyl)-piperidin-4-yl)-3,4-dihydro-2H-Benzo-b][1,4]oxazin-6-yl)-3-cyclopropyl-2-methylpropanoic acid.

Step B: Sodium Salt Formation

To a solution of (2S,3R)-methyl 3-((R or S)-3-(1-(2,5-bis (trifluoromethyl)-benzyl)piperidin-4-yl)-3,4-dihydro-2HBenzo-b][1,4]oxazin-6-yl)-3-cyclopropyl-2-methyl propanoic acid in acetonitrile (1 mL) was added aqueous NaOH (1.0 eq, 0.5 M), and the mixture was stirred at rt for 1 h. Then the mixture was lyophilized to give the title compound. MS (ESI) m/z: 571[M+H]$^+$. $^1$H NMR (400 MHz, Methanol-d$_4$): δ 8.20 (s, 1H), 7.88 (d, J=8.2 Hz, 1H), 7.74 (d, J=8.2 Hz, 1H), 6.59 (d, J=7.9 Hz, 1H), 6.51 (d, J=1.3 Hz, 1H), 6.40-6.31 (m, 1H), 4.17 (dd, J=2.2, 10.6 Hz, 1H), 3.99 (dd, J=6.4, 10.6 Hz, 1H), 3.72 (s, 2H), 3.13 (br. s., 1H), 2.92 (d, J=10.8 Hz, 2H), 2.73-2.63 (m, 1H), 2.18-2.06 (m, 2H), 1.91 (d, J=8.8 Hz, 1H), 1.83-1.73 (m, 2H), 1.57-1.44 (m, 3H), 1.08-0.97 (m, 1H), 0.90 (d, J=6.8 Hz, 3H), 0.60-0.48 (m, 1H), 0.35-0.23 (m, 2H), 0.03-0.08 (m, 1H).

TABLE 1

The compound of Example 3 was prepared according to the procedure of Example 2 starting from intermediate 34.

| Example | Structure | M.W. | Compound Name | LC/MS (ESI) observed [M + 1]+ |
|---|---|---|---|---|
| 3 | 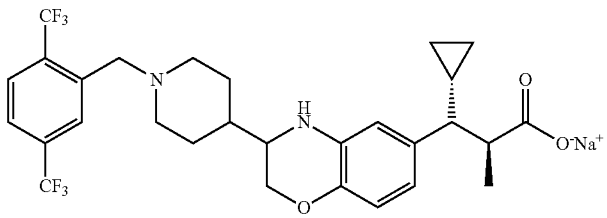 | 507.57 | Sodium (2S,3R)-methyl 3-((S or R)-3-(1-(2,5-bis(trifluoro-methyl)-benzyl)-piperidin-4-yl)-3,4-dihydro-2H-benzo[b]-[1,4]oxazin-6-yl)-3-cyclopropyl-2-methylpropanoate | 571.2 |

Example 4

Sodium (2S,3S)-3-((R or S)-3-(1-(2,5-bis(trifluoromethyl)benzyl)piperidin-4-yl)-4-methyl-3,4-dihydro-2H-benzo[b][1,4]oxazin-6-yl)-3-cyclopropyl-2-methylpropanoate

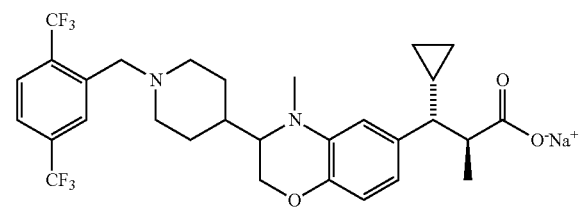

Step A: (2S,3R)-Methyl 3-((R or S)-3-(1-(2,5-bis(trifluoromethyl)benzyl)piperidin-4-yl)-4-methyl-3,4-dihydro-2H-benzo[b][1,4]oxazin-6-yl)-3-cyclopropyl-2-methylpropanoate To a solution of intermediate 33 (140 mg, 0.239 mmol) in MeOH (5 mL) was added paraformaldehyde (14.3 mg, 0.479 mmol), acetic acid (10 µL, 0.239 mmol), sodium cyanotrihydroborate (45.1 mg, 0.718 mmol) and water (10 µL, 0.239 mmol). The reaction was stirred at 25° C. for 15 h. Then the reaction was concentrated, and diluted with water (20 mL) and EtOAc (30 mL). The mixture was extracted with EtOAc (30 mL×3). The combined organic layers were washed with brine (30 mL), dried over anhydrous MgSO$_4$ and filtered. The filtrate was concentrated to give the title compound. MS (ESI) m/z: 599[M+H]$^+$.

Step B: (2S,3S)-3-((R or S)-3-(1-(2,5-bis(trifluoromethyl)benzyl)piperidin-4-yl)-4-methyl-3,4-dihydro-2H-benzo[b][1,4]oxazin-6-yl)-3-cyclopropyl-2-methylpropanoic acid (2S,3R)-Methyl 3-((R or S)-3-(1-(2,5-bis(trifluoromethyl)benzyl)piperidin-4-yl)-4-methyl-3,4-dihydro-2H-benzo[b][1,4]oxazin-6-yl)-3-cyclopropyl-2-methylpropanoate (170 mg, 0.284 mmol) was dissolved in MeOH (1.5 mL), THF (1.5 mL) and H$_2$O (1.5 mL) and treated with LiOH (136 mg, 5.68 mmol). The reaction was stirred at 50° C. for 44 h. Then the reaction mixture was acidified with saturated citric acid to adjust the pH to pH 5. The mixture was extracted with EtOAc (20 mL×3). The combined organic layers were washed with brine (40 mL), dried over anhydrous MgSO$_4$ and filtered. The filtrate was concentrated under reduced pressure. The resulting residue was purified by prep-HPLC (neutral) to give (2S,3S)-3-((R or S)-3-(1-(2,5-bis(trifluoromethyl)benzyl)piperidin-4-yl)-4-methyl-3,4-dihydro-2H-benzo[b][1,4]oxazin-6-yl)-3-cyclopropyl-2-methylpropanoic acid.

Step C: Sodium Salt Formation (2S,3S)-3-((R or S)-3-(1-(2,5-bis(trifluoromethyl)benzyl)-piperidin-4-yl)-4-methyl-3,4-dihydro-2H-benzo[b][1,4]-oxazin-6-yl)-3-cyclopropyl-2-methylpropanoic acid was dissolved in acetonitrile (1 mL) and treated with aqueous NaOH (1.0 eq, 0.5 M). The mixture was stirred at 20° C. for 1 h, then lyophilized to give the title compound. MS (ESI) m/z: 585.2 [M+H]$^+$. $^1$H NMR (400 MHz, Methanol-d$_4$): δ 8.19 (s, 1H), 7.86 (d, J=8.2 Hz, 1H), 7.73 (d, J=7.9 Hz, 1H), 6.62 (d, J=7.9 Hz, 1H), 6.45 (s, 1H), 6.35 (d, J=7.9 Hz, 1H), 4.33 (d, J=10.8 Hz, 1H), 3.78 (dd, J=1.8, 10.8 Hz, 1H), 3.71 (s, 2H), 3.05-2.98 (m, 4H), 2.89 (d, J=11.0 Hz, 2H), 2.78-2.66 (m, 1H), 2.13-2.00 (m, 2H), 1.89-1.62 (m, 4H), 1.50 (quin, J=11.8 Hz, 2H), 1.14-1.01 (m, 1H), 0.91 (d, J=6.6 Hz, 3H), 0.60-0.51 (m, 1H), 0.36-0.24 (m, 2H), 0.04-0.06 (m, 1H).

TABLE 2

The compound of Example 5 was prepared according to the procedure of Example 4 starting from intermediate 34.

| Example | Structure | M.W. | Compound Name | LC/MS (ESI) observed [M + 1]+ |
|---|---|---|---|---|
| 5 | 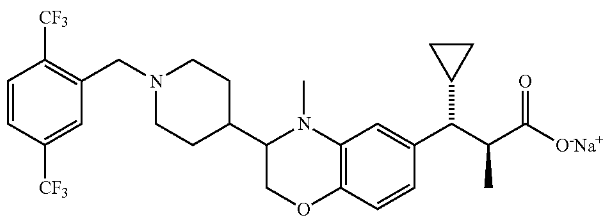 | 584.59 | Sodium (2S,3S)-3-((S or R)-3-(1-(2,5-bis(trifluoro-methyl)-benzyl)piperidin-4-yl)-4-methyl-3,4-dihydro-2H-benzo[b]-[1,4]oxazin-6-yl)-3-cyclopropyl-2-methyl propanoate | 585.2 |

Example 5

$^1$H NMR (400 MHz, Methanol-d$_4$): δ 8.19 (s, 1H), 7.87 (d, J=8.2 Hz, 1H), 7.73 (d, J=8.2 Hz, 1H), 6.63 (d, J=8.2 Hz, 1H), 6.44 (s, 1H), 6.38 (d, J=7.8 Hz, 1H), 4.33 (d, J=11.0 Hz, 1H), 3.79 (dd, J=2.0, 10.6 Hz, 1H), 3.70 (s, 2H), 3.06-2.98 (m, 4H), 2.88 (d, J=10.6 Hz, 2H), 2.75-2.64 (m, 1H), 2.11-1.98 (m, 2H), 1.85 (t, J=9.8 Hz, 1H), 1.80-1.62 (m, 3H), 1.50 (quin, J=12.0 Hz, 2H), 1.14-1.02 (m, 1H), 0.89 (d, J=7.0 Hz, 3H), 0.60-0.50 (m, 1H), 0.36-0.25 (m, 2H), 0.04-0.08 (m, 1H).

Example 6

Sodium (2S,3R)-3-((R or S)-2-(1-(2,5-bis(trifluoromethyl)benzyl)piperidin-4-yl)-1,2,3,4-tetrahydroquinolin-7-yl)-3-cyclopropyl-2-methylpropanoate

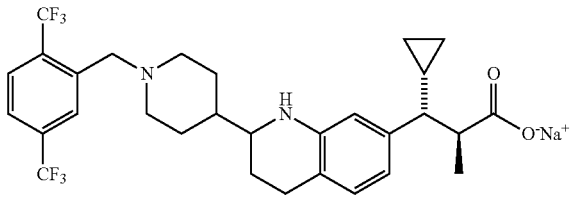

Step A: (2S,3R)-3-((R or S)-2-(1-(2,5-bis(trifluoromethyl)benzyl)piperidin-4-yl)-1,2,3,4-tetrahydroquinolin-7-yl)-3-cyclopropyl-2-methylpropanoic acid To a solution of Intermediate 20 (90.0 mg, 0.154 mmol) in MeOH (1.0 mL), THF (1.0 mL) and water (1.0 mL) was added LiOH (324 mg, 7.72 mmol). The mixture was stirred at 60° C. for 12 h, then ice (2.00 g) was added and the reaction mixture was treated with citric acid to adjust the pH to pH 8. The aqueous layer was extracted with EtOAc (10 mL×3). The combined organic layers were dried over sodium sulfate, and then filtered. The filtrate was concentrated under reduced pressure to give the crude product, which was purified by preparative-HPLC (0.05% ammonia hydroxide, v/v) to give the title compound.

Step B: Sodium Salt Formation

To (2S,3R)-3-((R or S)-2-(1-(2,5-bis(trifluoro-methyl)-benzyl)piperidin-4-yl)-1,2,3,4-tetrahydroquinolin-7-yl)-3-cyclopropyl-2-methylpropanoic acid was added MeCN (1.0 mL) and water (1.0 mL), followed by aqueous NaOH (1.0 eq, 0.5 M). The mixture was stirred for 1 h at rt, then lyophilized to give the sodium salt. LCMS (ESI) m/z: 569.2[M+H]+ $^1$H NMR (400 MHz, Methanol-d4): δ=8.24 (s, 1H), 7.92 (d, J=8.2 Hz, 1H), 7.78 (d, J=8.2 Hz, 1H), 6.84 (d, J=7.5 Hz, 1H), 6.45 (s, 1H), 6.40 (d, J=7.5 Hz, 1H), 3.77 (s, 2H), 3.08 (d, J=4.0 Hz, 1H), 2.97 (d, J=9.3 Hz, 2H), 2.80-2.69 (m, 3H), 2.16 (t, J=10.3 Hz, 2H), 2.01-1.68 (m, 5H), 1.50 (br. s., 3H), 1.13-1.02 (m, 1H), 0.94 (d, J=6.8 Hz, 3H), 0.62-0.50 (m, 1H), 0.39-0.25 (m, 2H), 0.07-0.04 (m, 1H).

TABLE 3

The compound of Example 7 was prepared according to the procedure of Example 6 starting from intermediate 19

| Example | Structure | M.W. | Compound Name | LC/MS (ESI) observed [M + 1]+ |
|---|---|---|---|---|
| 7 | 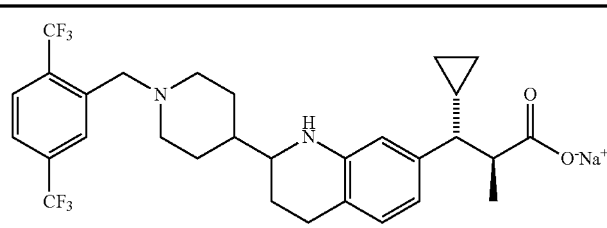 | 568.59 | Sodium (2S,3R)-3-((S or R)-2-(1-(2,5-bis(tri-fluoromethyl)-benzyl)-piperidin-4-yl)-1,2,3,4-tetrahydroquin-olin-7-yl)-3-cyclo-propyl-2-methyl propanoate | 569.2 |

Example 7

¹H NMR (400 MHz, Methanol-d₄): δ=8.20 (s, 1H), 7.88 (d, J=8.2 Hz, 1H), 7.74 (d, J=8.6 Hz, 1H), 6.80 (d, J=7.7 Hz, 1H), 6.41 (s, 1H), 6.35 (d, J=7.3 Hz, 1H), 3.73 (s, 2H), 3.04 (d, J=8.2 Hz, 1H), 2.93 (d, J=12.1 Hz, 2H), 2.77-2.63 (m, 3H), 2.12 (t, J=10.0 Hz, 2H), 1.97-1.65 (m, 5H), 1.46 (br. s., 3H), 1.04 (br. s., 1H), 0.90 (d, J=6.8 Hz, 3H), 0.54 (br. s., 1H), 0.27 (d, J=6.4 Hz, 2H), −0.03 (d, J=5.3 Hz, 1H).

Example 8

(2S,3R)-3-((R or S)-2-(1-(2,5-bis(trifluoromethyl)benzyl)piperidin-4-yl)-1-methyl-1,2,3,4-tetrahydroquinolin-7-yl)-3-cyclopropyl-2-methylpropanoic acid

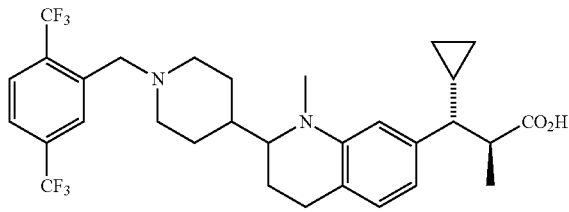 [SMILES: C[C@H](C(=O)O)[C@H](c1ccc2c(c1)N(C)C(C1CCN(Cc3cc(C(F)(F)F)ccc3C(F)(F)F)CC1)CC2)C1CC1]

To a solution of intermediate 21 (130 mg, 0.218 mmol) in MeOH (2.0 mL), THF (2.0 mL) and H₂O (2.0 mL) was added LiOH (274 mg, 6.54 mmol). The reaction mixture was stirred at 50° C. for 12 h. Then H₂O (3.0 mL) was added, followed by saturated citric acid to adjust the pH of the mixture to pH 6. The aqueous layer was extracted with EtOAc (10 mL×3). The combined organic layers were dried over sodium sulfate then filtered. The filtrate was concentrated under reduced pressure to give the crude product which was purified by preparative-HPLC (0.05% ammonia hydroxide, v/v) to give the title compound. LCMS (ESI) m/z: 583.2 [M+H]⁺ 1H NMR (400 MHz, Methanol-d₄): δ8.21 (s, 1H), 7.89 (d, J=8.2 Hz, 1H), 7.75 (d, J=8.2 Hz, 1H), 6.86 (d, J=7.5 Hz, 1H), 6.39 (d, J=7.5 Hz, 1H), 6.33 (s, 1H), 3.72 (br. s., 2H), 3.04 (s, 3H), 2.91 (d, J=11.0 Hz, 2H), 2.84-2.70 (m, 2H), 2.66-2.56 (m, 1H), 2.14-1.99 (m, 3H), 1.89-1.70 (m, 4H), 1.66-1.27 (m, 4H), 1.11 (br. s., 1H), 0.92 (d, J=6.8 Hz, 3H), 0.57 (d, J=7.5 Hz, 1H), 0.32 (d, J=5.1 Hz, 2H), 0.01 (br. s., 1H).

Example 9

¹H NMR (400 MHz, Methanol-d₄): δ 8.19 (s, 1H), 7.87 (d, J=8.2 Hz, 1H), 7.73 (d, J=7.9 Hz, 1H), 6.84 (d, J=7.5 Hz, 1H), 6.39-6.31 (m, 2H), 3.71 (s, 2H), 3.03 (s, 3H), 2.89 (d, J=11.0 Hz, 2H), 2.82-2.69 (m, 2H), 2.65-2.54 (m, 1H), 2.11-1.98 (m, 3H), 1.86-1.69 (m, 4H), 1.68-1.19 (m, 4H), 1.13-0.99 (m, 1H), 0.91 (d, J=6.8 Hz, 3H), 0.61-0.51 (m, 1H), 0.35-0.25 (m, 2H), 0.09 (m, 1H).

Example 10

(2S,3R)-3-Cyclopropyl-3-(2-(2'-fluoro-5'-methoxy-[1,1'-biphenyl]-4-yl)-1,2,3,4-tetrahydroquinolin-7-yl)-2-methylpropanoic acid

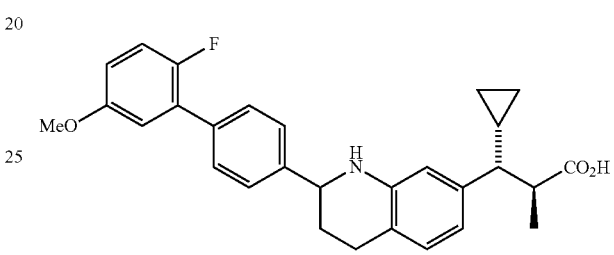

To a solution of intermediate 25 (400 mg, 0.845 mmol) in MeOH (3 mL), THF (2 mL) and water (3 mL) was added LiOH (202 mg, 8.45 mmol) at rt. The mixture was stirred at 50° C. for 18 h, then the mixture pH was adjusted to pH 6 with HCl (2M aqueous). The mixture was treated with water (10 mL) and EtOAc (10 mL). The organic layer was separated. The aqueous layer was extracted with EtOAc (10 mL×3). The combined organic layers were dried over anhydrous sodium sulfate, filtered and concentrated under reduced pressure to afford Example 10 as a mixture of diastereomers. ¹H NMR (400 MHz, MeOD): δ=7.50-7.44 (m, 4H), 7.07 (t, J=9.6 Hz, 1H), 6.95 (dd, J₁=3.1, J₂=6.3 Hz, 1H), 6.89-6.81 (m, 2H), 6.45 (s, 1H), 6.38 (d, J=7.4 Hz, 1H), 4.45 (dd, J₁=2.7, J₂=8.6 Hz, 1H), 3.79 (s, 3H), 2.90-2.80 (m, 1H), 2.76-2.61 (m, 2H), 2.11 (dd, J₁=3.5, J₂=12.5 Hz, 1H), 1.98-1.96 (m, 1H), 1.78 (t, J=10.0 Hz, 1H), 1.05 (br. s., 1H), 0.92 (d, J=6.7 Hz, 3H), 0.57-0.50 (m, 1H), 0.29 (t, J=6.1 Hz, 2H), 0.00 (d, J=3.9 Hz, 1H). MS (ESI) m/z: 460.2 [M+H]⁺.

TABLE 4

The compound of Example 9 was prepared according to the procedure of Example 8 starting from intermediate 19.

| Example | Structure | M.W. | Compound Name | LC/MS (ESI) observed [M + 1]⁺ |
|---|---|---|---|---|
| 9 | (structure shown) | 582.62 | (2S,3R)-3-((S or R)-2-(1-(2,5-bis(trifluoromethyl)-benzyl)piperidin-4-yl)-1-methyl-1,2,3,4-tetrahydroquinolin-7-yl)-3-cyclopropyl-2-methyl propanoic acid | 583.2 |

Examples 11 and 12

Sodium (2S,3R)-3-cyclopropyl-3-((R or S)-2-(2'-fluoro-5'-methoxy-[1,1'-biphenyl]-4-yl)-1,2,3,4-tetrahydroquinolin-7-yl)-2-methylpropanoate (Example 11); and (2S,3R)-3-cyclopropyl-3-((S or R)-2-(2'-fluoro-5'-methoxy-[1,1'-biphenyl]-4-yl)-1,2,3,4-tetrahydroquinolin-7-yl)-2-methylpropanoic acid (Example 12)

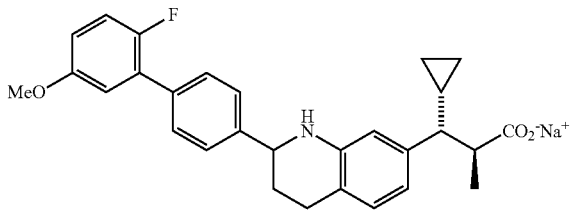

Step A: Chiral Separation

The compounds in the mixture of Example 10 (350 mg, 0.762 mmol) were separated by SFC (Instrument SFC-80-(8) Method Column OJ (250 mm*30 mm, 10 um) Condition Base-EtOH Begin B 45% End B 45% Gradient Time (min) 100% B Hold Time (min) Flow Rate (mL/min) 80 Injections 270) to give (2S,3R)-3-cyclopropyl-3-((R or S)-2-(2'-fluoro-5'-methoxy-[1,1'-biphenyl]-4-yl)-1,2,3,4-tetrahydro-quinolin-7-yl)-2-methylpropanoic acid (Example 11), and (2S,3R)-3-cyclopropyl-3-((S or R)-2-(2'-fluoro-5'-methoxy-[1,1'-biphenyl]-4-yl)-1,2,3,4-tetrahydroquinolin-7-yl)-2-methylpropanoic acid (Example 12).

Step B: Sodium Salt Formation

To a solution of the acid of the compound of Example 11 in CH$_3$CN (1.0 mL) and H$_2$O (1.0 mL) was added aqueous NaOH (1.0 eq, 0.5 M), and the mixture was stirred at 20° C. for 1 h. Then the mixture was lyophilized to give the sodium salt of the compound of Example 11. $^1$H NMR (400 MHz, CDCl$_3$): δ=7.57-7.52 (m, 2H), 7.51-7.45 (m, 2H), 7.08 (t, J=9.5 Hz, 1H), 6.95 (d, J=8.2 Hz, 2H), 6.87-6.80 (m, 1H), 6.49 (d, J=7.5 Hz, 1H), 6.37 (s, 1H), 4.48 (d, J=6.8 Hz, 1H), 3.83 (s, 3H), 3.02-2.89 (m, 1H), 2.86-2.72 (m, 2H), 2.21-2.11 (m, 1H), 1.86 (t, J=9.9 Hz, 1H), 1.49 (d, J=6.8 Hz, 1H), 1.11 (d, J=4.2 Hz, 1H), 1.03 (d, J=6.6 Hz, 3H), 0.68-0.57 (m, 1H), 0.38 (d, J=6.0 Hz, 2H), 0.08 (d, J=5.1 Hz, 1H).

TABLE 5

The sodium salt of the compound of Example 12 was prepared according to Step B of the procedure of Examples 11 and 12 starting from the free acid

| Example | Structure | M.W. | Compound Name | LC/MS (ESI) observed [M + 1]$^+$ |
|---|---|---|---|---|
| 12 | 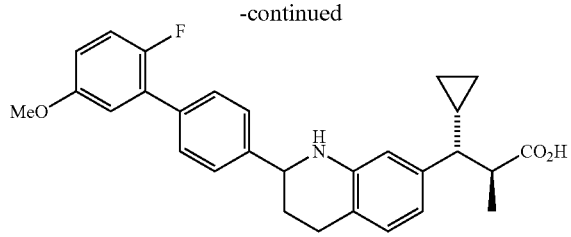 | 582.62 | Sodium (2S,3R)-3-((S or R)-2-(1-(2,5-bis(trifluoromethyl)-benzyl)piperidin-4-yl)-1-methyl-1,2,3,4-tetrahydroquinolin-7-yl)-3-cyclopropyl-2-methyl propanoate | 583.2 |

Example 12

$^1$H NMR (400 MHz, CDCl$_3$): δ=0.57-7.52 (m, 2H), 7.51-7.46 (m, 2H), 7.08 (t, J=9.4 Hz, 1H), 6.98-6.93 (m, 2H), 6.84 (td, J=3.2, 8.8 Hz, 1H), 6.50 (d, J=7.5 Hz, 1H), 6.37 (s, 1H), 4.48 (d, J=6.8 Hz, 1H), 3.83 (s, 3H), 3.01-2.89 (m, 1H), 2.86-2.72 (m, 2H), 2.20-2.12 (m, 1H), 2.10-1.99 (m, 1H), 1.86 (t, J=9.9 Hz, 1H), 1.49 (d, J=7.1 Hz, 1H), 1.11 (br. s., 1H), 1.04 (d, J=6.6 Hz, 3H), 0.67-0.57 (m, 1H), 0.38 (d, J=5.3 Hz, 2H), 0.08 (d, J=5.1 Hz, 1H).

Example 13

(2S,3R)-3-cyclopropyl-3-((RS)-2-(2'-fluoro-5'-methoxy-[1,1'-biphenyl]-4-yl)-1-methyl-1,2,3,4-tetrahydroquinolin-7-yl)-2-methylpropanoic acid

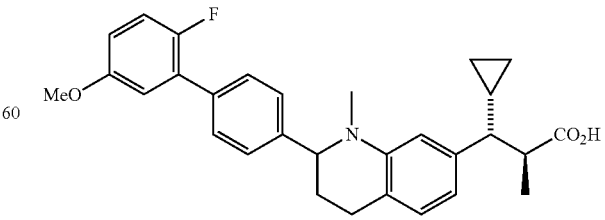

To a solution of intermediate 26 (200 mg, 0.410 mmol) in MeOH (2 mL), THF (2 mL) and water (1.5 mL) was added LiOH (98 mg, 4.10 mmol) at rt. The mixture was stirred at 50° C. for 24 h, then the pH of the mixture was adjusted to pH 6 with aqueous HCl (2 M). The mixture was treated with water (10 mL) and EtOAc (10 mL). The organic layer was separated. The aqueous layer was extracted with EtOAc (10 mL×3). The combined organic layers were dried over anhydrous sodium sulfate, filtered and concentrated under reduced pressure to give the title compound as a mixture of diastereomers. MS (ESI) m/z: 474.3 [M+H]⁺.

Examples 14 and 15

(2S,3R)-3-cyclopropyl-3-((R or S)-2-(2'-fluoro-5'-methoxy-[1,1'-biphenyl]-4-yl)-1-methyl-1,2,3,4-tetrahydroquinolin-7-yl)-2-methylpropanoic acid, and (2S,3R)-3-cyclopropyl-3-((S or R)-2-(2'-fluoro-5'-methoxy-[1,1'-biphenyl]-4-yl)-1-methyl-1,2,3,4-tetrahydroquinolin-7-yl)-2-methylpropanoic acid

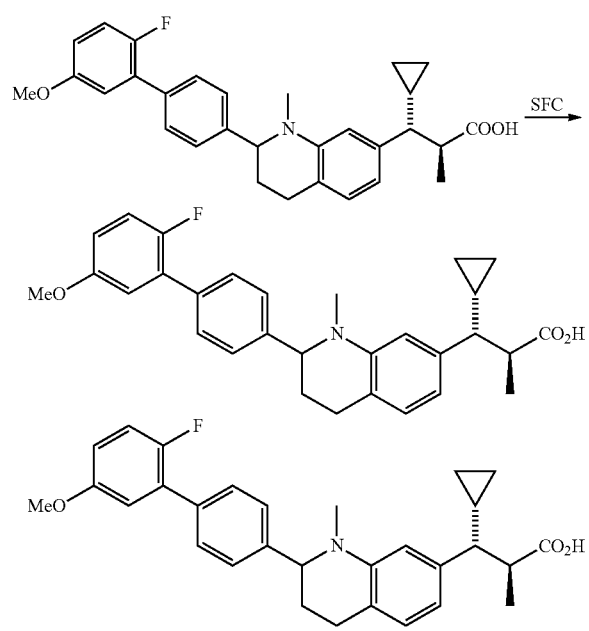

Chiral Separation

Example 13 (180 mg, 0.38 mmol) was separated by SFC ((Column AD (250 mm*30 mm, 10 um) Condition Base-EtOH Begin B 30% End B 30% Gradient Time (min) 100% B Hold Time (min) FlowRate (mL/min) 80 Injections 60) to give (2S,3R)-3-cyclopropyl-3-((R or S)-2-(2'-fluoro-5'-methoxy-[1,1'-biphenyl]-4-yl)-1-methyl-1,2,3,4-tetrahydroquinolin-7-yl)-2-methylpropanoic acid (Example 14), and (2S,3R)-3-cyclopropyl-3-((S or R)-2-(2'-fluoro-5'-methoxy-[1,1'-biphenyl]-4-yl)-1-methyl-1,2,3,4-tetrahydro-quinolin-7-yl)-2-methylpropanoic acid (Example 15).

Example 14

¹H NMR (400 MHz, CDCl₃): δ=7.50 (d, J=7.4 Hz, 1H), 7.25 (s, 2H), 7.07 (t, J=9.6 Hz, 1H), 6.97-6.90 (m, 2H), 6.82 (td, J=3.3, 8.6 Hz, 1H), 6.5-6.45 (m, 2H), 4.52 (t, J=4.1 Hz, 1H), 3.82 (s, 3H), 2.94-2.83 (m, 4H), 2.70-2.53 (m, 2H), 2.29-2.18 (m, 1H), 2.05 (dd, J₁=4.7, J₂=12.5 Hz, 1H), 1.95 (t, J=10.0 Hz, 1H), 1.24-1.15 (m, 1H), 1.07 (d, J=7.0 Hz, 3H), 0.70-0.59 (m, 1H), 0.41 (d, J=5.1 Hz, 2H), 0.14 (d, J=4.7 Hz, 1H). MS (ESI) m/z: 474.3 [M+H]⁺. Example 15: ¹H NMR (400 MHz, CDCl₃): δ=7.38 (d, J=7.4 Hz, 1H), 7.13 (d, J=8.2 Hz, 2H), 6.95 (t, J=9.6 Hz, 1H), 6.85-6.77 (m, 2H), 6.70 (td, J=3.5, 8.6 Hz, 1H), 6.39-6.32 (m, 2H), 4.40 (t, J=4.1 Hz, 1H), 3.70 (s, 3H), 2.77 (s, 4H), 2.58-2.42 (m, 2H), 2.15-2.04 (m, 1H), 1.97-1.88 (m, 1H), 1.83 (t, J=10.0 Hz, 1H), 1.10-1.01 (m, 1H), 0.94 (d, J=6.7 Hz, 3H), 0.57-0.47 (m, 1H), 0.34-0.24 (m, 2H), 0.02 (d, J=4.7 Hz, 1H). MS (ESI) m/z: 474.3 [M+H]⁺.

Example 16

(2S,3R)-3-cyclopropyl-3-((RS)-3-(2'-fluoro-5'-methoxy-[11'-biphenyl]-4-yl)-3,4-dihydro-2H-benzo[b][1,4]oxazin-6-yl)-2-methylpropanoic acid

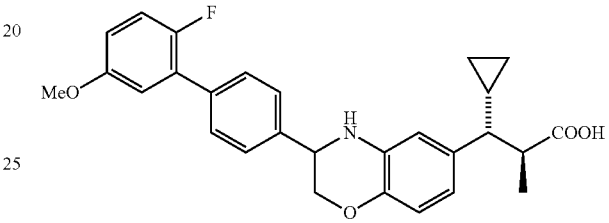

To a solution of Intermediate 31 (200 mg, 0.410 mmol) in MeOH (2 mL), THF (2 mL) and water (1.5 mL) was added LiOH (98 mg, 4.10 mmol) at rt. The mixture was stirred at 50° C. for 24 h, then the pH of the mixture was adjusted to pH=6 with aqueous HCl (2M). The mixture was diluted with water (10 mL) and EtOAc (10 mL). The organic layer was separated. The aqueous layer was extracted with EtOAc (10 mL×3). The combined organic layers were dried over anhydrous sodium sulfate, filtered and concentrated under reduced pressure to give the title compound as a mixture of diastereomers. MS (ESI) m/z: 474.3 [M+H]⁺.

Examples 17 and 18

Sodium (2S,3R)-3-cyclopropyl-3-((R or S)-3-(2'-fluoro-5'-methoxy-[1,1'-biphenyl]-4-yl)-3,4-dihydro-2H-benzo[b][1,4]oxazin-6-yl)-2-methyl propanoate; and Sodium (2S,3R)-3-cyclopropyl-3-((S or R)-3-(2'-fluoro-5'-methoxy-[1,1'-biphenyl]-4-yl)-3,4-dihydro-2H-benzo[b][1,4]oxazin-6-yl)-2-methyl propanoate

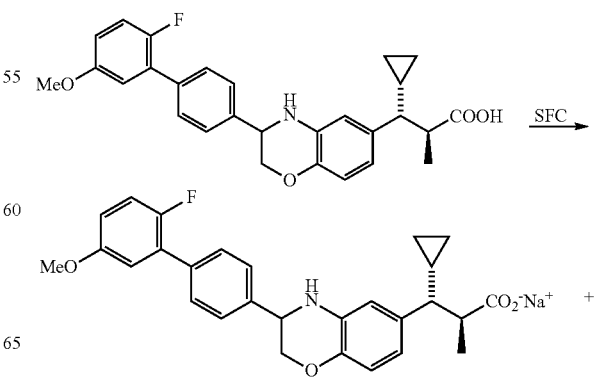

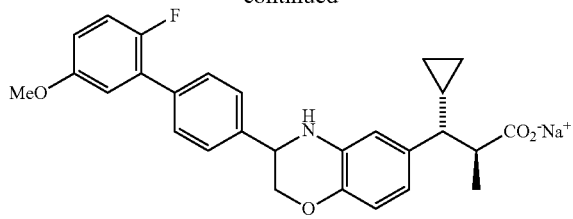

Step A: Chiral Separation

Example 16 (180 mg, 0.38 mmol) was separated by SFC (Column AD (250 mm*30 mm, 10 um) Condition Base-EtOH Begin B 30% End B 30% Gradient Time (min) 100% B Hold Time (min) FlowRate (mL/min) 80 Injections 60) to give (2S,3R)-3-cyclopropyl-3-((R or S)-3-(2'-fluoro-5'-methoxy-[1,1'-biphenyl]-4-yl)-3,4-dihydro-2H-benzo[b][1,4]oxazin-6-yl)-2-methylpropanoic acid (Example 17), and (2S,3R)-3-cyclopropyl-3-((S or R)-3-(2'-fluoro-5'-methoxy-[1,1'-biphenyl]-4-yl)-3,4-dihydro-2H-benzo[b][1,4]oxazin-6-yl)-2-methylpropanoic acid (Example 18).

Step B: Sodium Salt of Example 17

To a solution of Example 17 in $CH_3CN$ (1.0 mL) and $H_2O$ (1.0 mL) was added aqueous NaOH (1.0 eq, 0.5 M), then the mixture was stirred at rt for 1 h. The mixture was lyophilized to give the sodium salt of Example 17. $^1$H NMR (400 MHz, $CDCl_3$): δ=7.50 (d, J=7.4 Hz, 1H), 7.25 (s, 2H), 7.07 (t, J=9.6 Hz, 1H), 6.97-6.90 (m, 2H), 6.82 (td, J=3.3, 8.6 Hz, 1H), 6.51-6.45 (m, 2H), 4.52 (t, J=4.1 Hz, 1H), 3.82 (s, 3H), 2.94-2.83 (m, 4H), 2.70-2.53 (m, 2H), 2.29-2.18 (m, 1H), 2.05 (dd, $J_1$=4.7, $J_2$=12.5 Hz, 1H), 1.95 (t, J=10.0 Hz, 1H), 1.24-1.15 (m, 1H), 1.07 (d, J=7.0 Hz, 3H), 0.70-0.59 (m, 1H), 0.41 (d, J=5.1 Hz, 2H), 0.14 (d, J=4.7 Hz, 1H).

Step C: Sodium Salt of Example 18

The sodium salt of example 18 was prepared according to the procedure to make the sodium salt of Example 17. $^1$H NMR (400 MHz, $CDCl_3$): δ=7.38 (d, J=7.4 Hz, 1H), 7.13 (d, J=8.2 Hz, 2H), 6.95 (t, J=9.6 Hz, 1H), 6.85-6.77 (m, 2H), 6.70 (td, J=3.5, 8.6 Hz, 1H), 6.39-6.32 (m, 2H), 4.40 (t, J=4.1 Hz, 1H), 3.70 (s, 3H), 2.77 (s, 4H), 2.58-2.42 (m, 2H), 2.15-2.04 (m, 1H), 1.97-1.88 (m, 1H), 1.83 (t, J=10.0 Hz, 1H), 1.10-1.01 (m, 1H), 0.94 (d, J=6.7 Hz, 3H), 0.57-0.47 (m, 1H), 0.34-0.24 (m, 2H), 0.02 (d, J=4.7 Hz, 1H). MS (ESI) m/z: 474.3 [M+H]$^+$.

Example 19

(2S,3R)-3-Cyclopropyl-3-((RS)-3-(2'-fluoro-5'-methoxy-[1,1'-biphenyl]-4-yl)-4-methyl-3,4-dihydro-2H-benzo[b][1,4]oxazin-6-yl)-2-methylpropanoic acid

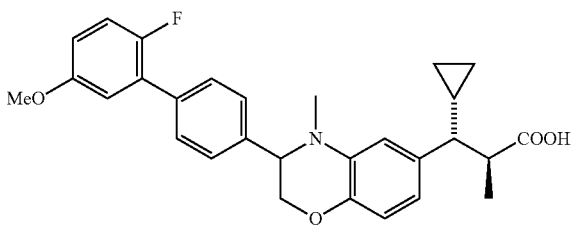 [SMILES: COc1ccc(F)c(-c2ccc(C3COc4ccc([C@H](C5CC5)[C@H](C)C(=O)O)cc4N3C)cc2)c1]

To a solution of intermediate 32 (150 mg, 0.306 mmol) in MeOH (1.5 mL), THF (1.5 mL) and $H_2O$ (1.5 mL) was added LiOH (73.4 mg, 3.06 mmol) at rt. The mixture was stirred at 50° C. for 18 h, then concentrated HCl was added to adjust the pH to pH 6. The resulting mixture was filtered. The filtrate was purified by preparative HPLC (Instrument ED Method; Column Phenomenex Synergi C18 250*21.2 mm*4 um; Conditions: water (0.05% $NH_4OH$ v/v)-ACN begin B 27 end B 47 gradient time (min); 10 100% B Hold Time (min) 2 Flow Rate (mL/min) 25 Injections 6) to give the title compound as a mixture of diastereomers. $^1$H NMR (400 MHz, $CDCl_3$): δ=7.56 (d, J=7.4 Hz, 2H), 7.36 (d, J=7.8 Hz, 2H), 7.08 (t, J=9.6 Hz, 1H), 6.95 (dd, $J_1$=2.9, $J_2$=6.1 Hz, 1H), 6.84 (td, J=3.2, 8.8 Hz, 1H), 6.78 (d, J=8.2 Hz, 1H), 6.60 (s, 1H), 6.51 (d, J=7.8 Hz, 1H), 4.36 (d, J=3.5 Hz, 1H), 4.32-4.24 (m, 1H), 4.21-4.12 (m, 1H), 3.83 (s, 3H), 2.90-2.77 (m, 4H), 1.94 (t, J=10.0 Hz, 1H), 1.14 (d, J=3.1 Hz, 1H), 1.05 (d, J=6.3 Hz, 3H), 0.68-0.60 (m, 1H), 0.46-0.34 (m, 2H), 0.11 (d, J=5.1 Hz, 1H). MS (ESI) m/z: 476.2 [M+H]$^+$.

Examples 20 and 21

Sodium (2S,3R)-3-cyclopropyl-3-((R or S)-3-(2'-fluoro-5'-methoxy-[1,1'-biphenyl]-4-yl)-4-methyl-3,4-dihydro-2H benzo-[b][1,4]oxazin-6-yl)-2-methyl propanoate; and Sodium (2S,3R)-3-cyclopropyl-3-((S or R)-3-(2'-fluoro-5'-methoxy-[1,1'-biphenyl]-4-yl)-4-methyl-3,4-dihydro-2H-benzo[b][1,4]oxazin-6-yl)-2-methyl propanoate

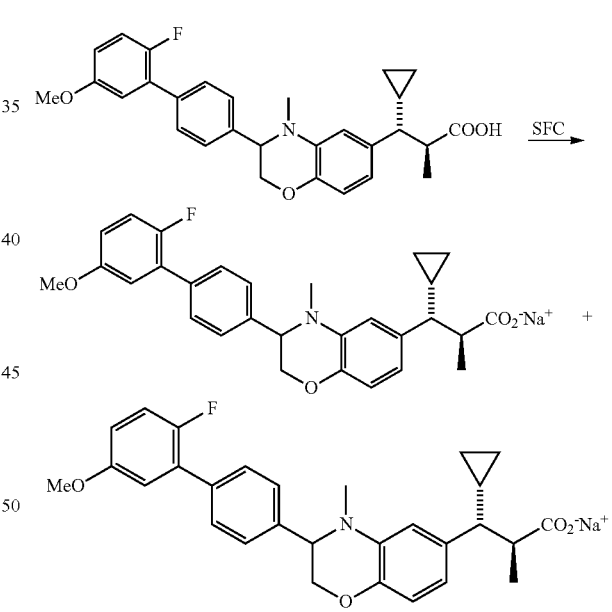

Step A: Chiral Separation (2S,3R)-3-cyclopropyl-3-((R or S)-3-(2'-fluoro-5'-methoxy-[1,1'-biphenyl]-4-yl)-4-methyl-3,4-dihydro-2H-benzo[b][1,4]oxazin-6-yl)-2-methylpropanoic acid (65 mg, 0.137 mmol, the compound of Example 19) was separated by SFC (Instrument SFC-80-(8) Method Column AD (250 mm*30 mm, 10 um) Condition Base-IPA Begin B 40% End B 40% Gradient Time (min) 100% B Hold Time (min) FlowRate (mL/min) 80 Injections 60) to give (2S,3R)-3-cyclopropyl-3-((R or S)-3-(2'-fluoro-5'-methoxy-[1,1'-biphenyl]-4-yl)-4-methyl-3,4-dihydro-2H-benzo[b][1,4]oxazin-6-yl)-2-methyl propanoic acid (Example 20), and (2S, 3R)-3-cyclopropyl-3-((S or R)-3-(2'-fluoro-5'-methoxy-[1,1'-biphenyl]-4-yl)-4-methyl-3,4-dihydro-2H-benzo[b][1,4]oxazin-6-yl)-2-methyl propanoic acid (Example 21).

Step B: Sodium Salt of Example 20

To a solution of Example 20 in $CH_3CN$ (1.0 mL) and $H_2O$ (1.0 mL) was added aqueous NaOH (1.0 eq, 0.5 M, 65 mg), then the mixture was stirred at rt for 1 h. The mixture was lyophilized to give Example 20 as the sodium salt. $^1H$ NMR (400 MHz, $CDCl_3$): δ=7.55 (d, J=7.0 Hz, 2H), 7.36 (d, J=8.2 Hz, 2H), 7.08 (t, J=9.6 Hz, 1H), 6.94 (dd, $J_1$=3.1, $J_2$=6.3 Hz, 1H), 6.84 (td, J=3.5, 8.7 Hz, 1H), 6.78 (d, J=7.8 Hz, 1H), 6.60 (s, 1H), 6.51 (d, J=7.8 Hz, 1H), 4.38-4.34 (m, 1H), 4.32-4.26 (m, 1H), 4.20-4.13 (m, 1H), 3.83 (s, 3H), 2.89-2.83 (m, 1H), 2.81 (s, 3H), 1.94 (t, J=9.8 Hz, 1H), 1.19-1.11 (m, 1H), 1.05 (d, J=6.7 Hz, 3H), 0.69-0.60 (m, 1H), 0.40 (d, J=5.1 Hz, 2H), 0.15-0.05 (m, 1H).

Step C: Sodium Salt of Example 21

The sodium salt of Example 21 was prepared according to the procedure to make the sodium salt of Example 20. $^1H$ NMR (400 MHz, MeOD): δ=7.58 (d, J=7.4 Hz, 2H), 7.42 (d, J=7.8 Hz, 2H), 7.14 (t, J=9.6 Hz, 1H), 7.05-7.00 (m, 1H), 6.97-6.90 (m, 1H), 6.73-6.67 (m, 2H), 6.51 (d, J=7.8 Hz, 1H), 4.43 (br. s., 1H), 4.34-4.27 (m, 1H), 4.22-4.14 (m, 1H), 3.86 (s, 3H), 2.87 (s, 3H), 2.67 (dd, J=7.0, 10.2 Hz, 1H), 1.97 (t, J=10.0 Hz, 1H), 1.19-1.09 (m, 1H), 0.92 (d, J=6.7 Hz, 3H), 0.59 (br. s., 1H), 0.47 (dd, $J_1$=4.5, $J_2$=8.8 Hz, 1H), 0.34-0.24 (m, 1H), 0.06-0.03 (m, 1H). LCMS: m/z 476.2 $[M+H]^+$ Example of a Pharmaceutical Composition As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:

Human GPR40 stable cell-lines were generated in HEK cells. The expression plasmids were transfected using lipofectamine (Life Technologies) following manufacturer's instructions. Stable cell-lines were generated following drug selection and single cell cloning.

Inositol Phosphate Turnover (IP1) Assay:

The assay was performed in 384-well format. HEK cells stably expressing human GPR40 were plated at 7500 cells per well in growth medium (DMEM/10% fetal calf serum). Cell plates were then incubated 16 hours at 37 degrees in a 5% $CO_2$ incubator. Measurement of Inositol Phosphate Turnover (IP1) was performed using the CisBio IP-One kit (Part number 62IPAPEB). After the 16 hour incubation, the growth media was removed by centrifugation using the BlueWasher (AusWasher GUI Ver. v1.0.1.8) Protocol #21- "Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% $CO_2$ incubator. 10 ul of detection buffer (also prepared as described in the IP-One kit) was added to each well and the plates were incubated at room temperature for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Data was normalized to % activity using a reference compound and EC50s determined using a standard 4-paramter fit.

The compounds of the present invention, including the compounds in Examples 1-21, have $EC_{50}$ values less than 6000 nanomolar (nM) in the Inositol Phophate Turnover Assay 1 described above. Inositol Phophate Turnover (IP1) Assay 1 $EC_{50}$ values for specific compounds are shown in Table 1.

TABLE I

| Example No. | Compound | Human IP1 $EC_{50}$ (nM) |
|---|---|---|
| 1 | 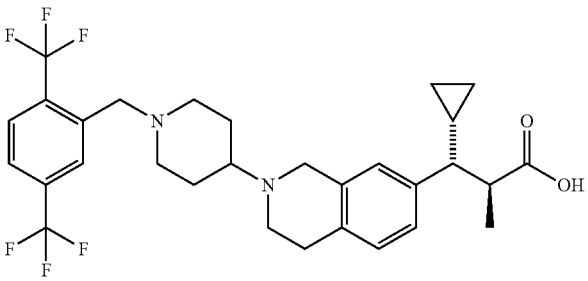 [SMILES: C[C@H](C(=O)O)[C@H](c1ccc2c(c1)CN(C1CCN(Cc3cc(C(F)(F)F)ccc3C(F)(F)F)CC1)CC2)C1CC1] | 611 |

TABLE I-continued

| Example No. | Compound | Human IP1 EC$_{50}$ (nM) |
|---|---|---|
| 2 | Isomer A | 388 |
| 3 | Isomer B | 642 |
| 4 | Isomer A | 4700 |
| 5 | Isomer B | 2095 |
| 6 | Isomer A | 35 |

TABLE I-continued
| Example No. | Compound | Human IP1 EC$_{50}$ (nM) |
|---|---|---|
| 7 | 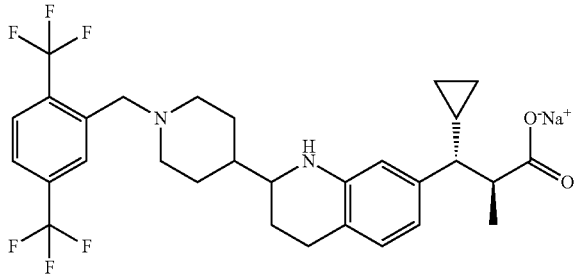
Isomer B | 99 |
| 8 | 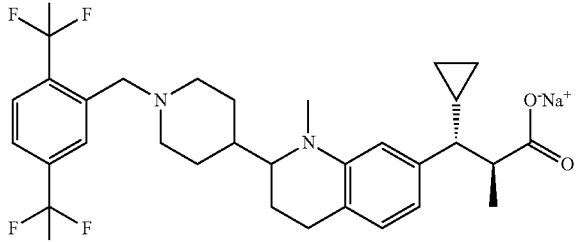
Isomer A | 439 |
| 9 | 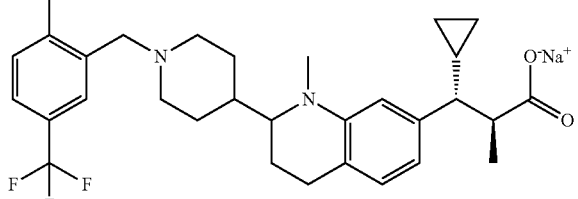
Isomer B | 289 |
| 11 | 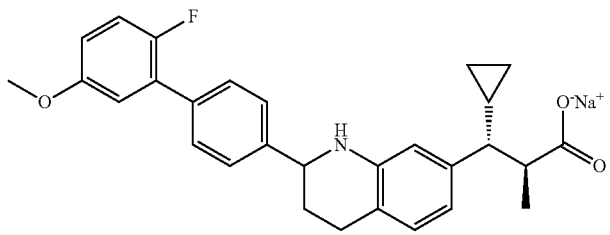
Isomer A | 0.79 |
| 12 | 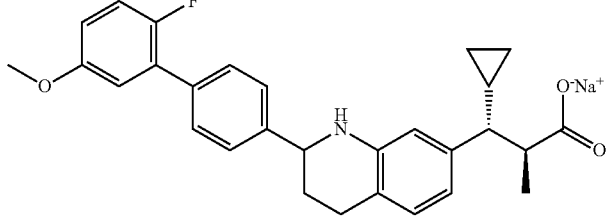
Isomer B | 0.2 |

TABLE I-continued

| Example No. | Compound | Human IP1 EC$_{50}$ (nM) |
|---|---|---|
| 14 | Isomer A | 1.0 |
| 15 | Isomer B | 12 |
| 17 | Isomer A | 10 |
| 18 | Isomer B | 0.8 |
| 20 | Isomer A | 0.8 |

TABLE I-continued

| Example No. | Compound | Human IP1 EC$_{50}$ (nM) |
|---|---|---|
| 21 | 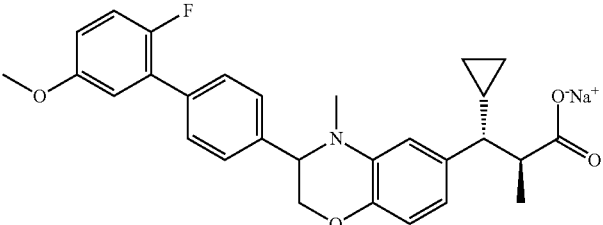 Isomer B | 12 |

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

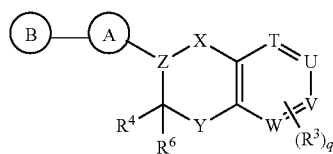

I wherein
T is CH;
U is CR$^1$;
V is CR$^2$;
W is CH;
X is N(R$^e$);
Y is selected from the group consisting of:
  (1) oxygen,
  (2) C(R$^g$)(R$^g$), and
  (3) N(R$^c$);
Z is C(R$^5$);
A is selected from the group consisting of:
  (1) aryl,
  (2) heteroaryl,
  (3) C$_{3-8}$cycloalkyl, and
  (4) C$_{2-7}$cycloheteroalkyl,
wherein A is unsubstituted or substituted with one to five substituents selected from Ra;
B is selected from the group consisting of:
  (1) aryl,
  (2) aryl-O—,
  (3) aryl-C$_{1-10}$ alkyl-,
  (4) aryl-C$_{1-10}$ alkyl-O—,
  (5) heteroaryl,
  (6) heteroaryl-O—,
  (7) heteroaryl-C$_{1-10}$ alkyl-, and
  (8) heteroaryl-C$_{1-10}$ alkyl-O—,
wherein B is unsubstituted or substituted with one to five substituents selected from R$^b$;
R$^1$ and R$^2$ are each independently selected from:
  (1) hydrogen,
  (2) —C$_{1-6}$alkyl, and
  (3) —C$_{3-6}$cycloalkyl,
wherein each alkyl and cycloalkyl is substituted with a substituent selected from R$^7$ and with one to three substituents selected from R$^9$, provided that one of R$^1$ and R$^2$ is C$_{1-6}$alkyl or C$_{3-6}$ cycloalkyl;
each R$^3$ is independently selected from the group consisting of:
  (1) hydrogen, and
  (2) F;
R$^4$ is selected from the group consisting of:
  (1) hydrogen,
  (2) halogen, and
  (3) C$_{1-6}$alkyl,
wherein alkyl is unsubstituted or substituted with one to three substituents selected from Rh;
R$^5$ is selected from the group consisting of:
  (1) hydrogen, and
  (2) —C$_{1-6}$alkyl, wherein alkyl is unsubstituted or substituted with one to three substituents selected from Rh;

$R^6$ is selected from the group consisting of:
(1) hydrogen, and
(2) —$C_{1-6}$alkyl, wherein alkyl is unsubstituted or substituted with one to three substituents selected from $R^h$;

$R^7$ is selected from the group consisting of:
(1) —$CO_2R^8$, and
(2) —$C_{1-6}$alkyl-$CO_2R^8$;

$R^8$ is selected from the group consisting of:
(1) hydrogen, and
(2) —$C_{1-6}$alkyl, wherein alkyl is unsubstituted or substituted with one to three substituents selected from $R^1$;

each $R^9$ is independently selected from the group consisting of:
(1) —$CO_2C_{1-6}$alkyl,
(2) —$C_{1-10}$alkyl,
(3) —$C_{2-10}$ alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl, wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$ alkyl;

each $R^a$ is selected from the group consisting of:
(1) —$C_{1-6}$alkyl,
(2) halogen,
(3) —$C_{3-6}$cycloalkyl,
(4) —$C_{2-5}$ cycloheteroalkyl, and
(5) —$C_{1-6}$alkyl-$N(R^j)(R^k)$, wherein each alkyl, cycloalkyl and cycloheteroalkyl is unsubstituted or substituted with one to three substituents independently selected from —$C_{1-6}$alkyl, halogen, —O—$C_{1-6}$alkyl, and —$CF_3$;

each $R^b$ is independently selected from the group consisting of:
(1) —$C_{1-10}$alkyl,
(2) —$CF_3$,
(3) halogen,
(4) —CN,
(5) —OH, and
(6) —$OC_{1-10}$alkyl, wherein each alkyl is unsubstituted or substituted with one to three substituents independently selected from —$C_{1-6}$alkyl, halogen, —O—$C_{1-6}$alkyl and —$CF_3$;

$R^c$ is independently selected from the group consisting of:
(1) hydrogen,
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl, and
(7) $C_{2-5}$ cycloheteroalkyl-$C_{1-10}$alkyl-, wherein alkyl, alkenyl, cycloalkyl, and cycloheteroalkyl is unsubstituted or substituted with one to three substituents independently selected from $R^f$;

each $R^d$ is selected from the group consisting of:
(1) hydrogen,
(2) —$C_{1-4}$alkyl, and
(3) halogen, wherein each alkyl is unsubstituted or substituted with one to five halogens;

$R^e$ is selected from the group consisting of:
(1) hydrogen, and
(2) —$C_{1-6}$alkyl, wherein alkyl is unsubstituted or substituted with one to three substituents selected from —$C_{1-6}$ alkyl, —$OC_{1-6}$alkyl, —$CF_3$ and halogen;

each $R^f$ is selected from the group consisting of:
(1) —$C_{1-4}$alkyl,
(2) —$OC_{1-4}$alkyl, and
(3) halogen, each $R^g$ is selected from the group consisting of:
(1) hydrogen,
(2) —$C_{1-4}$alkyl, and
(3) halogen, wherein each alkyl is unsubstituted or substituted with one to five halogens;

each $R^h$ is independently selected from the group consisting of:
(1) —$C_{1-6}$alkyl,
(2) —$OC_{1-6}$alkyl, and
(3) halogen;

each $R^i$ is independently selected from the group consisting of:
(1) —$C_{1-6}$ alkyl,
(2) —$OC_{1-6}$alkyl, and
(3) halogen;

$R^j$ and $R^k$ are each independently selected from the group consisting of:
(1) hydrogen
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl, and
(7) $C_{2-5}$cycloheteroalkyl-$C_{1-10}$alkyl-, wherein each alkyl, alkenyl, cycloalkyl, and cycloheteroalkyl is unsubstituted or substituted with one to three substituents independently selected from $C_{1-6}$alkyl, halogen, or —O—$C_{1-6}$alkyl; and q is independently selected from: 0, 1, 2 or 3;

or a pharmaceutically acceptable salt thereof.

2. The compound according to claim 1 wherein Y is selected from the group consisting of:
(1) oxygen, and
(2) $C(R^g)(R^g)$;
or a pharmaceutically acceptable salt thereof.

3. The compound according to claim 1 wherein A is selected from the group consisting of:
(1) aryl, and
(2) $C_{2-7}$cycloheteroalkyl,
wherein aryl and cycloheteroalkyl are unsubstituted or substituted with one to five substituents selected from $R^a$; or a pharmaceutically acceptable salt thereof.

4. The compound according to claim 1 wherein A is aryl, wherein aryl is unsubstituted or substituted with one to five substituents selected from $R^a$; or a pharmaceutically acceptable salt thereof.

5. The compound according to claim 1 wherein B is selected from the group consisting of:
(1) aryl, and
(2) aryl-$C_{1-10}$ alkyl-,
wherein B is unsubstituted or substituted with one to five substituents selected from Rb; or a pharmaceutically acceptable salt thereof.

6. The compound according to claim 1 wherein B is aryl, wherein aryl is unsubstituted or substituted with one to five substituents selected from Rb; or a pharmaceutically acceptable salt thereof.

7. The compound according to claim 1 wherein $R^1$ and $R^2$ are each independently selected from:
(1) hydrogen, and
(2) —$C_{1-6}$ alkyl,
wherein each alkyl is substituted with a substituent selected from $R^7$ and with one to three substituents selected from $R^9$, provided that one of $R^1$ and $R^2$ is —$C_{1-6}$alkyl; or a pharmaceutically acceptable salt thereof.

8. The compound according to claim 1 wherein $R^1$ is —$C_{1-6}$alkyl, wherein alkyl is substituted with a substituent selected from $R^7$ and with one to three substituents selected from $R^9$; and
$R^2$ is hydrogen;
or a pharmaceutically acceptable salt thereof.

9. The compound according to claim 1 wherein $R^3$ is hydrogen; $R^4$ is hydrogen; $R^5$ is hydrogen; and $R^6$ is hydrogen; or a pharmaceutically acceptable salt thereof.

10. The compound according to claim 1 wherein $R^7$ is —$CO_2R^8$; or a pharmaceutically acceptable salt thereof.

11. The compound according to claim 1 wherein $R^8$ is hydrogen; or a pharmaceutically acceptable salt thereof.

12. The compound according to claim 1 wherein each $R^9$ is independently selected from the group consisting of:
(1) —$C_{1-10}$alkyl, and
(2) —$C_{3-6}$cycloalkyl,
wherein alkyl and cycloalkyl is unsubstituted or substituted with 1-4 substituents selected from $C_{1-6}$alkyl, halogen, and —$OC_{1-6}$alkyl;
or a pharmaceutically acceptable salt thereof.

13. The compound according to claim 1 of structural Formula Id:

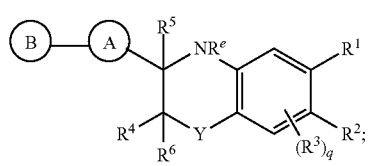

wherein
Y is selected from the group consisting of:
(1) oxygen, and
(2) $C(R^g)(R^g)$;
A is selected from the group consisting of:
(1) aryl, and
(2) $C_{2-7}$cycloheteroalkyl,
wherein aryl and cycloheteroalkyl are unsubstituted or substituted with one to five substituents selected from $R^a$;
B is selected from the group consisting of:
(1) aryl, and
(2) aryl-$C_{1-10}$ alkyl-,
wherein B is unsubstituted or substituted with one to five substituents selected from $R^b$;
$R^1$ and $R^2$ are each independently selected from:
(1) hydrogen, and
(2) —$C_{1-6}$ alkyl,
wherein each alkyl is substituted with a substituent selected from $R^7$ and with one to three substituents selected from $R^9$, provided that one of $R^1$ and $R^2$ is $C_{1-6}$alkyl;

$R^3$, $R^4$, $R^5$, $R^6$, and $R^8$ are hydrogen;
$R^7$ is —$CO_2R^8$;
each $R^9$ is independently selected from the group consisting of:
(1) —$C_{1-10}$alkyl, and
(2) —$C_{3-6}$cycloalkyl,
wherein each alkyl and cycloalkyl is unsubstituted or substituted with 1-4 substituents selected from $C_{1-6}$alkyl, halogen, and —$OC_{1-6}$alkyl; and
$R^e$ is selected from the group consisting of:
(1) hydrogen, and
(2) —$C_{1-6}$alkyl,
wherein each alkyl is unsubstituted or substituted with one to three substituents selected from —$C_{1-6}$ alkyl, —$OC_{1-6}$alkyl, —$CF_3$ and halogen;
q is 1;
or a pharmaceutically acceptable salt thereof.

14. The compound according to claim 1 of structural Formula Ie:

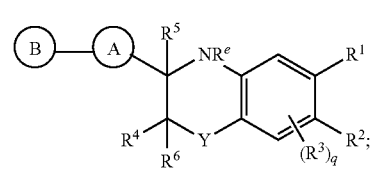

wherein
Y is selected from the group consisting of:
(1) oxygen, and
(2) $C(R^g)(R^g)$;
A is aryl, wherein aryl is unsubstituted or substituted with one to five substituents selected from $R^a$;
B is aryl, wherein aryl is unsubstituted or substituted with one to five substituents selected from $R^b$;
$R^1$ is —$C_{1-6}$alkyl, wherein alkyl is substituted with a substituent selected from $R^7$ and with one to three substituents selected from $R^9$;
$R^2$, $R^3$, $R^4$, $R^5$, $R^6$, and $R^8$ are hydrogen;
$R^7$ is —$CO_2R^8$;
each $R^9$ is independently selected from the group consisting of:
(1) —$C_{1-10}$alkyl, and
(2) —$C_{3-6}$cycloalkyl,
wherein each alkyl and cycloalkyl is unsubstituted or substituted with 1-4 substituents selected from $C_{1-6}$alkyl, halogen, and —$OC_{1-6}$alkyl;
$R^e$ is selected from the group consisting of:
(1) hydrogen, and
(2) —$C_{1-6}$alkyl,; and
q is 1;
or a pharmaceutically acceptable salt thereof.

15. The compound according to claim 1 selected from:

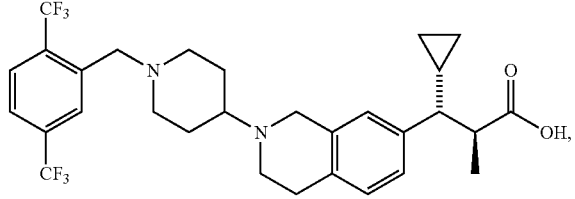

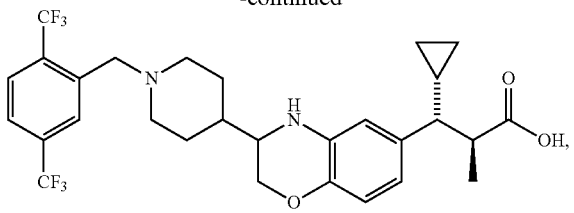
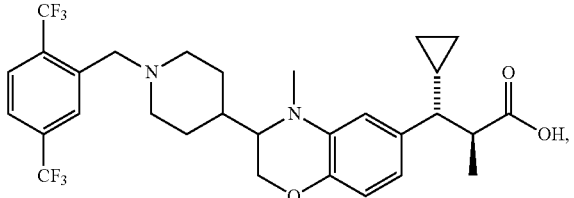
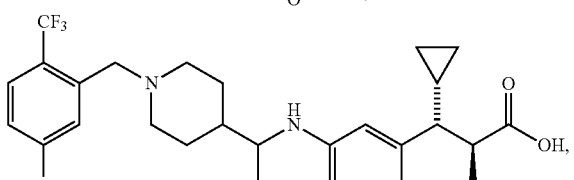
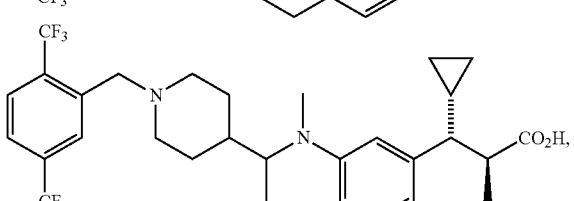
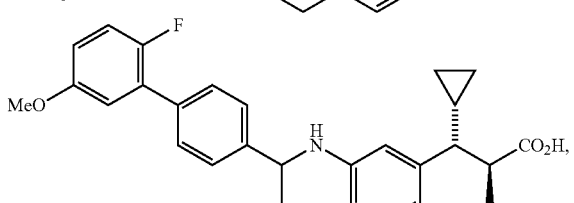
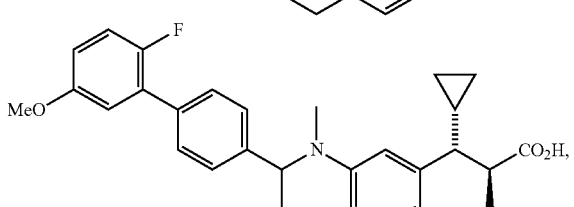
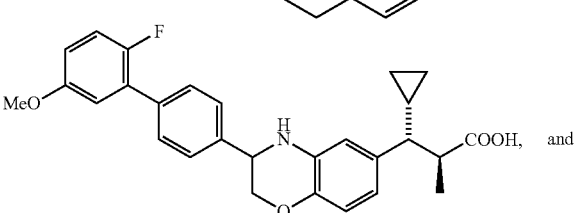

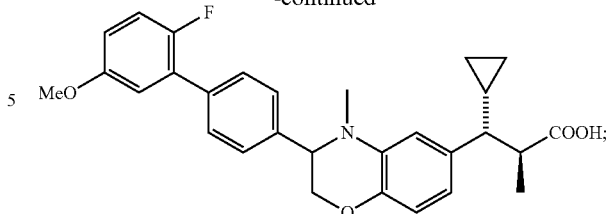

or a pharmaceutically acceptable salt thereof.

16. A pharmaceutical composition comprising a compound of claim 1, or a pharmaceutically acceptable salt thereof, and a pharmaceutically acceptable carrier.

17. A pharmaceutical composition comprising
(1) a compound of claim 1, or a pharmaceutically acceptable salt thereof;
(2) one or more compounds selected from the group consisting of:
(a) PPAR gamma agonists and partial agonists;
(b) biguanides;
(c) protein tyrosine phosphatase-1B (PTP-1B) inhibitors;
(d) dipeptidyl peptidase IV (DP-IV) inhibitors;
(e) insulin or an insulin mimetic;
(f) sulfonylureas;
(g) α-glucosidase inhibitors;
(h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA: cholesterol acyltransferase (ACAT) inhibitors, (vii) CETP inhibitors, and (viii) phenolic anti-oxidants;
(i) PPARα/γ dual agonists,
(j) PPARδ agonists,
(k) antiobesity compounds,
(l) ileal bile acid transporter inhibitors;
(m) anti-inflammatory agents;
(n) glucagon receptor antagonists;
(o) GLP-1;
(p) GIP-1;
(q) GLP-1 analogs;
(r) HSD-1 inhibitors;
(s) SGLT-2 inhibitors; and
(t) SGLT-1/SGLT-2 inhibitors; and
(3) a pharmaceutically acceptable carrier.

18. A pharmaceutical composition comprising a compound according to claim 1, or a pharmaceutically acceptable salt thereof, and a compound selected from simvastatin, ezetimibe and sitagliptin; and a pharmaceutically acceptable carrier.

* * * * *